(12) United States Patent
Edwards et al.

(10) Patent No.: US 9,816,135 B2
(45) Date of Patent: Nov. 14, 2017

(54) FLUIDIC CARTRIDGE FOR NUCLEIC ACID AMPLIFICATION AND DETECTION

(71) Applicant: Atlas Genetics Limited, Trowbridge, Wiltshire (GB)

(72) Inventors: Thomas Richard Kerby Edwards, Wiltshire (GB); Toby Charles Edward Mullarkey, Wiltshire (GB); Kevin David Neale, Wiltshire (GB); Jay Kendall Taylor, Ottawa (CA); Ben Arlett, Bristol (GB)

(73) Assignee: Atlas Genetics Limited, Trowbridge, Wiltshire (GB)

( * ) Notice: Subject to any disclaimer, the term of this patent is extended or adjusted under 35 U.S.C. 154(b) by 0 days.

(21) Appl. No.: 14/906,636

(22) PCT Filed: Jul. 28, 2014

(86) PCT No.: PCT/GB2014/052301
§ 371 (c)(1),
(2) Date: Jan. 21, 2016

(87) PCT Pub. No.: WO2015/015175
PCT Pub. Date: Feb. 5, 2015

(65) Prior Publication Data
US 2016/0168624 A1    Jun. 16, 2016

(30) Foreign Application Priority Data
Jul. 29, 2013   (GB) .................................. 1313511.6

(51) Int. Cl.
| C12M 1/00 | (2006.01) |
| C12P 19/34 | (2006.01) |
| C12Q 1/68 | (2006.01) |
| B01L 3/00 | (2006.01) |
| G01N 27/403 | (2006.01) |
| B01L 7/00 | (2006.01) |

(52) U.S. Cl.
CPC .............. *C12Q 1/686* (2013.01); *B01L 3/502* (2013.01); *B01L 3/502738* (2013.01); *C12Q 1/6825* (2013.01); *G01N 27/403* (2013.01); *B01L 7/52* (2013.01); *B01L 2200/10* (2013.01); *B01L 2200/16* (2013.01); *B01L 2300/0645* (2013.01); *B01L 2300/0681* (2013.01); *B01L 2300/0816* (2013.01); *B01L 2300/0867* (2013.01); *B01L 2300/0877* (2013.01); *B01L 2300/0883* (2013.01); *B01L 2400/0481* (2013.01); *B01L 2400/0487* (2013.01); *B01L 2400/06* (2013.01); *B01L 2400/0638* (2013.01); *B01L 2400/0683* (2013.01)

(58) Field of Classification Search
CPC .............. B01L 2200/10; B01L 2200/16; B01L 2300/0645; B01L 2300/0681; B01L 2300/0816; B01L 2300/0867; B01L 2300/0877; B01L 2300/0883; B01L 2400/0481; B01L 2400/0487; B01L 2400/06; B01L 2400/0638; B01L 2400/0683
USPC .............................................. 435/283.1, 91.2
See application file for complete search history.

(56) References Cited

U.S. PATENT DOCUMENTS

| 7,482,733 | B2 | 1/2009 | Weber |
| 7,595,871 | B2 | 9/2009 | Weber |
| 7,771,176 | B2 | 8/2010 | Weber |
| 8,759,081 | B2 | 6/2014 | Klaunick et al. |
| 8,783,488 | B2 | 7/2014 | Weber |
| 8,950,424 | B2 | 2/2015 | Weber et al. |
| 8,960,230 | B2 | 2/2015 | Weber |
| 9,005,546 | B2 | 4/2015 | Weber |
| 9,108,192 | B2 | 8/2015 | Weber et al. |
| 9,149,802 | B2 | 10/2015 | Weber |
| 9,211,538 | B2 | 12/2015 | Weber |
| 2006/0140782 | A1 | 6/2006 | Weber |
| 2006/0215155 | A1 | 9/2006 | Weber |
| 2007/0007859 | A1 | 1/2007 | Weber |
| 2010/0308051 | A1 | 12/2010 | Weber |
| 2011/0297866 | A1 | 12/2011 | Weber |
| 2011/0303306 | A1 | 12/2011 | Weber |
| 2012/0082599 | A1 | 4/2012 | Weber |
| 2012/0115738 | A1* | 5/2012 | Zhou ..................... B01F 5/0683 506/9 |
| 2012/0178179 | A1 | 7/2012 | Kim et al. |
| 2012/0187117 | A1 | 7/2012 | Weber |
| 2013/0023060 | A1 | 1/2013 | Klaunik et al. |

(Continued)

FOREIGN PATENT DOCUMENTS

| AT | 359443 T | 5/2007 |
| AU | 2003266350 A1 | 4/2004 |
| CN | 105517710 A | 4/2016 |
| DE | 10242110 A1 | 3/2004 |
| DE | 20313727 U1 | 1/2005 |
| DE | 20315371 U1 | 2/2005 |
| DE | 10336849 A1 | 3/2005 |
| DE | 10336850 B4 | 10/2006 |
| DE | 102006031475 A1 | 1/2008 |
| DE | 102007051487 A1 | 4/2009 |
| DE | 102007059533 A1 | 6/2009 |
| DE | 202009008052 U1 | 8/2009 |

(Continued)

OTHER PUBLICATIONS

Lee et al., J. Micromech. Microeng. 15(2005) 1215-1223.*

(Continued)

*Primary Examiner* — Cynthia B Wilder
(74) *Attorney, Agent, or Firm* — Mintz Levin Cohn Ferris Glovsky and Popeo, P.C.

(57) ABSTRACT

A cartridge for assay of a target nucleic acid sequence in a liquid sample. The cartridge comprises: a fluidic portion through which the sample flows and in which nucleic acid amplification and detection takes place; a pneumatic portion which controls flow through the fluidic portion; and at least two electrodes which provide a potential difference for the detection of an amplified nucleic acid of interest.

20 Claims, 16 Drawing Sheets

(56) References Cited

U.S. PATENT DOCUMENTS

| | | |
|---|---|---|
| 2013/0087226 A1 | 4/2013 | Weber |
| 2013/0118621 A1 | 5/2013 | Weber et al. |
| 2013/0217026 A1 | 8/2013 | Egan et al. |
| 2013/0263940 A1 | 10/2013 | Weber |
| 2014/0000735 A1 | 1/2014 | Weber et al. |
| 2015/0290642 A1 | 10/2015 | Weber |
| 2016/0167047 A1 | 6/2016 | Weber et al. |
| 2016/0207041 A1 | 7/2016 | Weber |

FOREIGN PATENT DOCUMENTS

| | | |
|---|---|---|
| DE | 102009005874 A1 | 7/2010 |
| DE | 102009009728 A1 | 9/2010 |
| DE | 102009015395 A1 | 9/2010 |
| DE | 102009032744 A1 | 1/2011 |
| DE | 112011102117 A5 | 4/2013 |
| DE | 102011015184 B4 | 11/2013 |
| DE | 102012112306 A1 | 6/2014 |
| DK | 1552148 T3 | 8/2007 |
| EP | 1654065 A1 | 5/2006 |
| EP | 1661190 A1 | 5/2006 |
| EP | 1702684 A2 | 9/2006 |
| EP | 1552148 B1 | 4/2007 |
| EP | 1769848 A2 | 4/2007 |
| EP | 2041547 A2 | 4/2009 |
| EP | 2225037 A1 | 9/2010 |
| EP | 2437890 A1 | 4/2012 |
| EP | 2576065 A1 | 4/2013 |
| EP | 2647435 A1 | 10/2013 |
| EP | 2398589 B1 | 3/2014 |
| EP | 2454170 B1 | 8/2014 |
| EP | 2821138 A1 | 1/2015 |
| EP | 2851121 A1 | 3/2015 |
| EP | 2576068 B1 | 4/2015 |
| EP | 2679307 B1 | 8/2015 |
| EP | 2931429 A1 | 10/2015 |
| EP | 2962758 A1 | 1/2016 |
| EP | 2389529 B1 | 3/2016 |
| FR | 2967362 A1 | 5/2012 |
| JP | 2007501940 A | 2/2007 |
| JP | 4640549 B2 | 3/2011 |
| WO | WO-03074731 A2 | 9/2003 |
| WO | WO-2004031580 A1 | 4/2004 |
| WO | WO-2005016529 A1 | 2/2005 |
| WO | WO-2005024967 A1 | 3/2005 |
| WO | WO-2007/106579 A2 | 9/2007 |
| WO | WO-2008003312 A2 | 1/2008 |
| WO | WO-2009052805 A2 | 4/2009 |
| WO | WO-2009071078 A1 | 6/2009 |
| WO | WO-2010083795 A1 | 7/2010 |
| WO | WO-2010094249 A1 | 8/2010 |
| WO | WO-2010139295 A1 | 12/2010 |
| WO | WO-2011006460 A1 | 1/2011 |
| WO | WO-2011/106315 A1 | 9/2011 |
| WO | WO-2012019599 A2 | 2/2012 |
| WO | WO-2012048685 A1 | 4/2012 |
| WO | WO-2012/085591 A1 | 6/2012 |
| WO | WO-2013/190328 A1 | 12/2013 |
| WO | WO-2014090225 A1 | 6/2014 |
| WO | WO-2015001070 A1 | 1/2015 |
| WO | WO-2015039934 A1 | 3/2015 |
| WO | WO-2016000998 A1 | 1/2016 |
| WO | WO-2016000999 A1 | 1/2016 |

OTHER PUBLICATIONS

Hillier et al., An electrochemical study of enzymatic oligonucleotide digestion. Bioelectrochemistry. Jun. 2004;63(1-2):307-10.

Ihara et al., Ferrocene-oligonucleotide conjugates for electrochemical probing of DNA. Nucleic Acids Res. Nov. 1, 1996;24(21):4273-80.

\* cited by examiner

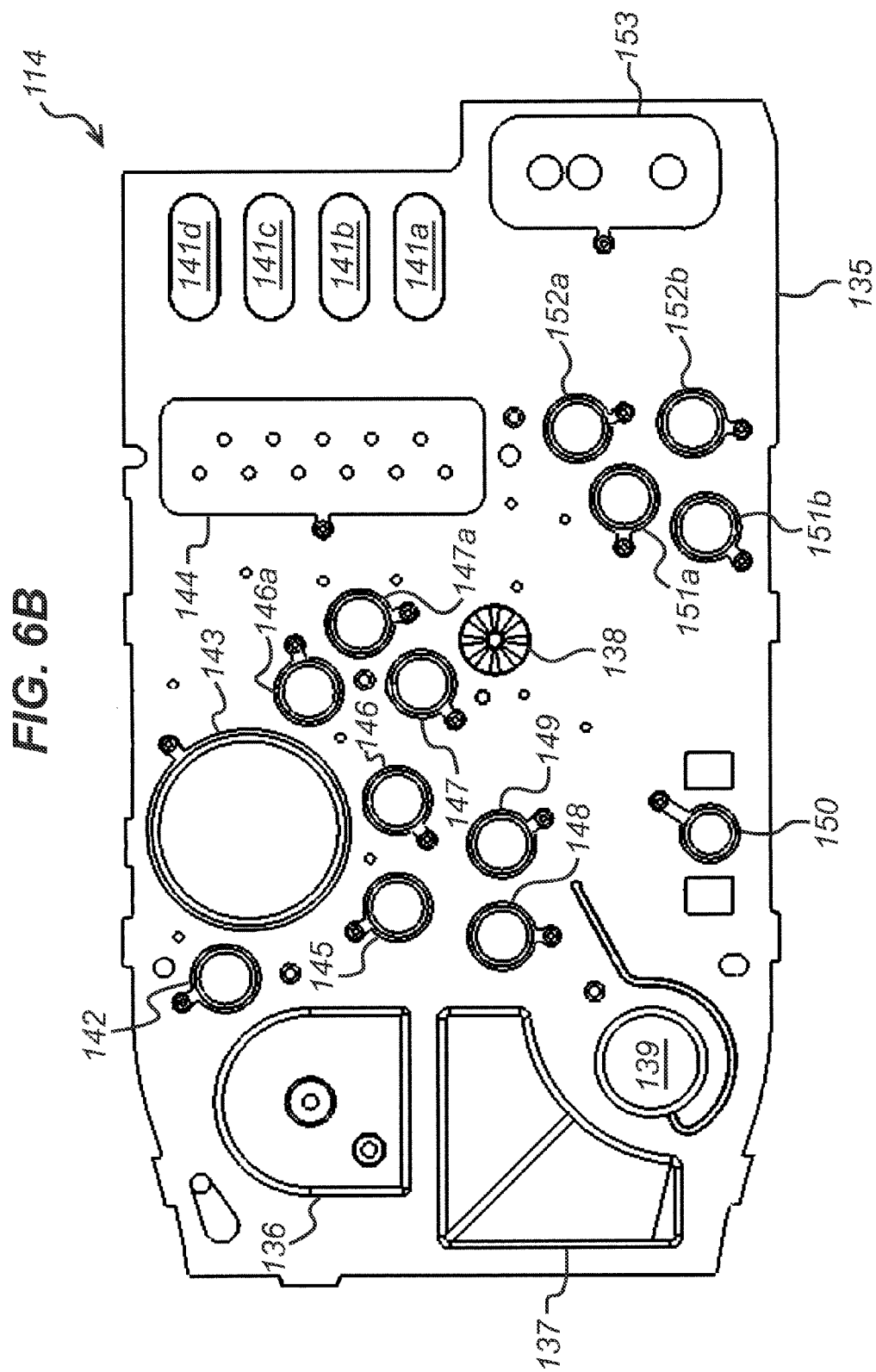

FLUIDIC CARTRIDGE FOR NUCLEIC ACID AMPLIFICATION AND DETECTION

CROSS-REFERENCES TO RELATED APPLICATIONS

This application is a national stage application, filed under 35 U.S.C. §371, of International Application No. PCT/GB2014/052301, filed on Jul. 28, 2014, and claims the benefit of, and priority to GB Patent Application No. 1313511.6, filed Jul. 29, 2013, the contents of each of which are incorporated hereby by reference in its entirety and for all purposes.

FIELD

The present invention relates to a fluidic cartridge for nucleic acid amplification and detection, more particularly where the fluidic cartridge comprises the reagents necessary for nucleic acid amplification and detection.

BACKGROUND

Sample preparation and analysis presents many logistical problems. Conventionally, many medical samples (such as blood, saliva, urine and swab eluate) are provided to a doctor, for example a general practitioner doctor (GP) or a principle care physician (PCP), in a local surgery without the equipment necessary to analyse the sample. Hence, the sample must be sent to a laboratory where the sample is analysed. The test results must then be collated and returned to the GP to analyse the results and make a diagnosis. This approach is inadequate. Firstly, there is a significant risk that a sample is lost in transit or mismatched with the wrong patient. Moreover, whilst recent developments in technology have reduced the overall time taken to conduct the test, the delay involved in sending the sample to a laboratory is unsatisfactory.

Nevertheless, analytical systems of the kind found in laboratories are complex and it is often difficult to provide sufficient amounts of pure targets from source samples to reliably perform downstream analytical assays. This typically prohibits local GP surgeries from being able to carry out such tests on site.

However, in recent years efforts have been made to reduce the scale of the analytical systems to make tests faster and simpler to run, and require smaller quantities of sample. For instance, "laboratory on a chip" (LOC) devices (a subset of microfluidic devices) integrate almost all medical tests or diagnostic operations performed in a hospital on a single microfluidic chip. The channels forming such microfluidics devices handle small fluid volumes and are connected together so as to achieve a desired function such as mixing of a sample, moving the sample through the device, reacting the sample with different reagents, and so on. These chips may be inserted into machines to control the performance of a test and measure the results.

However, it has been found that handling a sample in a microfluidics device can be very difficult. In such small channels as are found on a conventional LOC, it is difficult to apply external forces to move the sample from one site to another to perform different actions on the sample. There is also a limit to the complexity of a LOC device which operates purely using capillary action. Furthermore, owing to the small sample sizes of LOC's, the devices have reduced sensitivity and the probability of a target being present in the sample is thus reduced.

An alternative approach is to use a fluidic cartridge. The scale of the components of a fluidic cartridge is larger than for a microfluidic device, and so it becomes possible to move a sample through various different sites to perform different actions on it. This makes it possible to perform more complex tests than may be conducted using typical LOC devices, whilst still providing an analytical system of potential use in a local GP surgery.

Scientific assays useful in medical diagnostics have increasingly involved biochemical procedures, such as the polymerase chain reaction ("PCR"). The PCR assay has provided a powerful method of assaying for the presence of defined segments of nucleic acids. It is therefore desirable to perform a PCR assay on a fluidic cartridge.

Reducing PCR to the microchip level is important for portable detection technologies and high-throughput analytical systems. The method can be used to assay body fluids for the presence of nucleic acid specific for particular pathogens, such as the *Chlamydia trachomatis* bacterium, HIV or any other pathogenic microbe.

The introduction of commercially available automated DNA amplification assays has allowed more laboratories to introduce these technologies for routine testing of specimens. However, there is a need to improve the fluidic devices used for this purpose.

SUMMARY

The invention provides a cartridge for assay of a target nucleic acid sequence in a liquid sample comprising a plastic housing enclosing:
  a. a plastic fluidic portion comprising a channel fluidly connecting a sample inlet to at least one amplification chamber where nucleic acid amplification can take place; a channel fluidly connecting the amplification chamber to at least one detection chamber where the results of nucleic acid amplification can be detected; an exhaust; and a gas inlet connected to a gas supply which is capable of pushing the sample downstream through the cartridge,
  wherein the channels and/or chambers comprise at least one pneumatically controlled valve,
  and wherein upstream of the amplification chamber are provided: reagents and/or physical components for cell lysis and nucleic acid separation; in or upstream of the amplification chamber, but downstream of the reagents and/or physical components for cell lysis and nucleic acid separation, are provided reagents for nucleic acid amplification including a nucleic acid polymerase; and in or upstream of the detection chamber, but downstream of the amplification chamber, are provided reagents for nucleic acid detection;
  b. a plastic pneumatic portion comprising at least one pneumatic pressure inlet and pneumatic circuit for conveying pneumatic pressure;
  whereby flow through the channels and chambers can be controlled by the pneumatic pressure applied to the at least one pneumatically controlled valve; and
  c. at least two electrodes capable of providing a potential difference across the at least one detection chamber for permitting detection of electrochemically active molecules.

BRIEF DESCRIPTION OF THE FIGURES

FIG. 6B is a bottom view of the pneumatic layer of the exemplary fluidic cartridge of FIG. 2.

FIG. 13b is a perspective section view of the inlet port arrangement of FIG. 13a.

FIG. 14b is a perspective section view of a portion of the capture column arrangement of FIG. 14a.

FIG. 15b is a perspective section view of the waste chamber arrangement of FIG. 15a.

DETAILED DESCRIPTION

Figure 1:
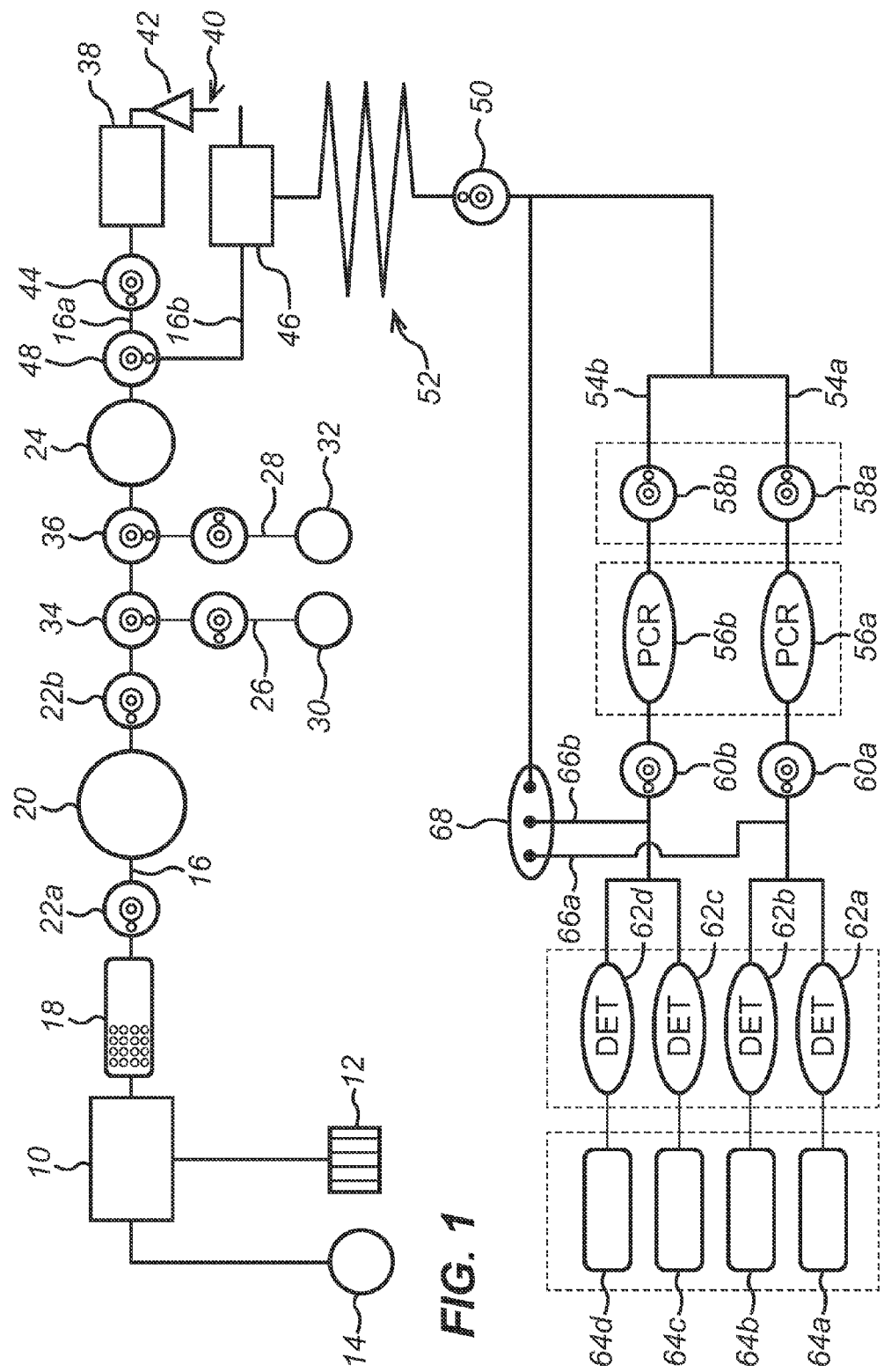
FIG. 1 is a schematic diagram of an exemplary fluidic cartridge in which the invention may be provided.

The cartridge of the invention comprises: a fluidic portion through which the sample flows and in which nucleic acid amplification and detection take place; a pneumatic portion which controls flow through the fluidic portion; and at least two electrodes which provide a potential difference for the detection of an amplified nucleic acid of interest. The fluidic portion and pneumatic portion may be constructed of a fluidic layer, a fluidic foil, a pneumatic layer and a pneumatic foil such as those described in relation to the exemplary cartridge below. However, the fluidic portion does not necessarily consist only of a fluidic layer and a fluidic foil and the pneumatic portion does not necessarily consist only of a pneumatic layer and a pneumatic foil. Rather, the layers may interact to produce the fluidic portion and the pneumatic portion such that parts of all or some of the layers make up each portion. Rather than referring to the particular layers of the cartridge, the fluidic portion refers to the particular areas of the cartridge which provide the function of allowing controlled sample flow, and the pneumatic portion refers to the particular areas of the cartridge which provide the function of controlling the flow through the fluidic portion.

The housing, fluidic portion and pneumatic portion are made of plastic. By plastic is meant a synthetic or natural organic material that may be shaped when soft and then hardened, including resins, resinoids, polymers, cellulose derivatives, casein materials, and protein plastics. Examples of plastics from which the cartridge may be constructed include, but are not limited to thermoplastics, for example polycarbonate, polyethylene terephthalate, cyclic olefin copolymers such as Topaz, acrylonitrile butadiene styrene, and thermoplastic elastomers, for example polypropylene. Plastic housings, fluidic portions and pneumatic portions can include components which are not made of plastic (e.g. blisters made from metal foil, metallic inserts at the sample inlet), but they are formed primarily from plastic. The use of plastic materials facilitates economical manufacture of the cartridges.

Whilst the pneumatic and fluidic foils may be made from a metal foil, the preferred materials are plastic including those mentioned above. In particular, it is preferred that foils are a polyethylene terephthalate/polypropylene composite.

The target nucleic acid sequence is any nucleic acid to be detected in a sample. The target nucleic acid(s) to be amplified and detected in the cartridge will usually be DNA, but it is also possible to amplify and detect RNA. In some embodiments a cartridge may permit amplification and/or detection of both DNA and RNA targets.

The liquid sample is the composition which is introduced into the cartridge in order to determine whether the target nucleic acid(s) of interest is/are present. The sample may be a composition in which the nucleic acid to be detected is suspected to be present (e.g. for clinical diagnosis), or may be a composition in which the nucleic acid to be detected is potentially present (e.g. for contamination testing).

The liquid sample can have various sources. For instance, it can be material obtained from an animal or plant (e.g. for diagnosis of infections or for genotyping). Such samples may be obtained with minimal invasiveness or non-invasively, e.g., the sample may be obtained from an animal using a swab, or may be a bodily fluid. As an alternative, the sample may be material obtained from food or water (e.g. for contamination testing). The sample will usually include cells, and the target nucleic acid (if present) can be extracted from these cells within the cartridge. One skilled in the art will appreciate that samples can be diluted or otherwise treated prior to being introduced into the cartridge, but it is preferred that the cartridge can handle material which has not been pre-treated in this way.

An animal from whom the sample is obtained may be a vertebrate or non-vertebrate animal. Vertebrate animals may be mammals. Examples of mammals include but are not limited to mouse, rat, pig, dog, cat, rabbit, primates or the like. The animal may be a primate, and is preferably a human. Thus the cartridge can be used for clinical diagnosis of human samples.

In addition to analysing a sample, the cartridge can analyse a positive and/or negative control to provide confirmation that the cartridge is functioning as expected. The control(s) can be introduced into the cartridge by a user, or can be included within a cartridge before use.

The inclusion of an internal positive control nucleic acid allows a user to identify whether a negative result for the sample has been obtained because the nucleic acid amplification has been unsuccessful (false negative). If the positive control nucleic acid fails to be detected in the detection chamber, despite its presence in an amplification chamber, the user will be able to identify the test as a potential false negative result, and can perform another test.

The inclusion of an internal negative control allows a user to identify whether a positive result has been falsely obtained because of the presence of contamination. A negative control can involve performing PCR in a chamber in which no nucleic acid is provided, or in which a sample undergoes an amplification reaction without necessary components e.g. PCR without primers. If nucleic acid is nevertheless detected in the detection chamber, despite its intended absence in an amplification chamber, the user will be able to identify the test as a potential false positive result, and can perform another test.

A positive control nucleic acid may be any nucleic acid that will not be found in a sample used in the cartridge. The internal control DNA may be taken from a bacterium that is not pathogenic to animals and which contains a nucleic acid that is highly specific to the bacterium. One example of a possible bacterium from which the control nucleic acid may be taken for an animal sample is *Pectobacterium atrosepticum*, although any control nucleic acid may be used that will not be present in a sample.

The fluidic portion of the cartridge comprises channels and chambers through which sample flows. The flow of sample through the cartridge is controlled in two ways. Firstly, the fluidic portion has a gas inlet. The gas inlet is connected to a gas supply, and injection of gas into the fluidic portion via this inlet allows the sample to be pushed downstream through the cartridge, towards the detection chamber. The gas supply may be provided by the reader. As an alternative, the gas supply may be an on-board gas supply. Preferably, the gas supply is provided by an external source and the gas inlet is connected to a pneumatic circuit such that the gas supply is provided via a pneumatic inlet on the cartridge. Secondly, at least one pneumatically controlled valve controls local movement of the sample through the fluidic portion. The pneumatically controlled valve(s) may be controlled independently of other pneumatically controlled valves and may be controlled independently of the gas supply that generally causes downstream movement of the sample via the gas inlet. The gas inlet and the pneumatically controlled valve(s) also permit sample to be flushed through the fluidic portion e.g. to exclude excess volumes of material. The fluidic portion also has an exhaust which allows air and waste material to exit the channels and chambers of the fluidic portion without a build-up of pressure occurring in the cartridge. Preferably, the exhaust comprises a waste chamber and/or a waste vent.

The fluidic portion of the cartridge includes reagents and/or physical components for cell lysis and nucleic acid separation. These may be any reagents or physical components that are capable of lysing cells and separating nucleic acids from cell debris and other cellular components. For instance, they may comprise (i) a lysis buffer which is capable of causing lysis of target cells which may be present in the sample e.g. buffers including a detergent such as nonyl phenoxypolyethoxylethanol (available as NP-40) or t-octyl-phenoxypolyethoxyethanol, (available as Triton X 100), or including guanidine thiocyanate, and/or (ii) a capture support or column which specifically binds nucleic acids but does not bind other undesired cellular components (e.g. proteins and lipids). The capture column comprises a capture filter and may additionally comprise a depth filter. The filters may be made of glass fibres (available as Whatman filters), or may be made of silica, although any column or support which is capable of separating nucleic acids from other cellular components may be used. Elution using a wash buffer to remove cell debris and other cellular components, followed by elution using an elution buffer to elute the separated nucleic acids from the capture support or column can be undertaken such that the capture column can separate nucleic acids from cell debris and other cellular components.

A channel through which the sample flows fluidly connects the sample inlet to at least one amplification chamber where nucleic acid amplification can take place. The purpose of the amplification chamber(s) is to permit amplification of any target nucleic acid of interest that is present in the sample (and, where present, any positive control nucleic acid). Any nucleic acid amplification method may be used and these are described in more detail below in relation to an exemplary cartridge. The different nucleic acid amplification reagents that are required for different nucleic acid amplification methods are well known in the art. These reagents are provided in or upstream of the amplification chamber(s) such that the sample (and any positive control) includes all necessary reagents for nucleic acid amplification once it reaches the amplification chamber. Adaptation of a nucleic acid amplification method according to the target nucleic acid to be detected is also well known in the art (e.g. design of primers). The skilled person would therefore be able to adapt the reagents for nucleic acid amplification accordingly. The term "chamber" does not denote any particular size or geometry, but instead it means a region within the fluidic portion which is designed to permit nucleic acid amplification to occur. Thus, for instance, it could be a region in which the sample can be fluidically isolated (e.g. via the use of pneumatically controlled valves) while the steps required for nucleic acid amplification (e.g. thermocycling, etc.) occur, and it can be located within the cartridge so that it is in the proximity of any external resources that are needed (e.g. next to a heat source within a cartridge reader, thereby permitting thermal cycling to occur).

Multiple test amplification channels and/or chambers may be included in the cartridge. The different test amplification channels and/or chambers may include reagents required to amplify different nucleic acids of interest. Therefore using multiple amplification test channels and/or chambers allows multiple tests to be performed on a single cartridge, simultaneously (including any controls). As an alternative, reagents for amplification of multiple different nucleic acids may be present in a single amplification chamber, and the different nucleic acids (whether multiple target nucleic acids, or a target nucleic acid and a control nucleic acid) may be amplified simultaneously in the same amplification chamber.

A further channel through which the sample flows after nucleic acid amplification fluidly connects the at least one amplification chamber to at least one detection chamber where the results of nucleic acid amplification can be detected. In or upstream of the detection chamber are reagents for nucleic acid detection such that the sample includes all necessary reagents for the detection once it reaches the detection chamber. The reagents for nucleic acid detection may be specific for the particular target nucleic acid, i.e. they may allow for detection of the presence of the specific nucleic acid sequence. As an alternative, the reagents for nucleic acid detection may be generic reagents to detect the presence of any nucleic acids. Such generic reagents may be used if all nucleic acids other than the target nucleic acid are removed prior to detection. For example, this may be achieved by providing a nuclease that is capable of hydrolysing all nucleic acids present in the sample other than the target nucleic. The amplified target nucleic acid can be protected from hydrolysis, for example by inclusion of chemical modifications in the primers which are incorporated into the amplified product and which cannot be hydrolysed. Reagents for nucleic acid detection are described below in relation to an exemplary cartridge but usually comprise a probe including a label. The probe is capable of hybridising to the amplified nucleic acid which has been amplified in the amplification chamber(s). Following hybridisation of the probe to the amplified nucleic acid, the detection of the nucleic acid may occur via a detectable change in the signal from the label. In some embodiments the change may be caused by hydrolysis of the probe. Where the probe is hydrolysed, hydrolysis is usually achieved using a double strand specific nuclease, which can be an exonuclease or an endonuclease. Preferably, the nuclease is T7 endonuclease. The signal from the label is capable of undergoing a change following hydrolysis of the probe. This is due to a change in the environment of the label when it moves from being bound to the rest of the probe to being free from the rest of the probe or bound to a single nucleotide or a short part of the probe. Further details of the types of probes and detection methods that may be used can be found in Hillier et al. Bioelectrochemistry, 63 (2004), 307-310. As an alternative, methods for causing a detectable change in the signal from the label which do not rely on hydrolysis of the probe may be used e.g. see Ihara et al. Nucleic Acids Research, 1996, Vol. 24, No. 21 4273-4280. This change in environment of the label leads to a change in the signal from the label. The change in signal from the label can be detected in order to detect the presence of the nucleic acid of interest.

Where a positive control nucleic acid is used, the reagents for nucleic acid detection will additionally include a positive control probe including a label. The positive control probe is capable of hybridising to the amplified control nucleic acid. The signal provided by the labels of the positive control and target probes may be the same, but present in separate detection chambers such that the signals corresponding to the control and test nucleic acids can be distinguished. As an alternative, the signal provided by the labels of the control and target probes may be different, such that the signals are distinguishable from one another, even if the probes are present in the same detection chamber.

Multiple test detection channels and/or chambers may be included in the cartridge. The different test detection channels and/or chambers may include reagents required to detect different nucleic acids of interest. Therefore using multiple detection test channels and/or chambers allows multiple tests to be performed on a single cartridge, simultaneously. As an alternative, reagents for detection of multiple different nucleic acids may be present in a single detection chamber, and the different nucleic acids (whether multiple target nucleic acids or a target nucleic acid and a control nucleic acid) may be detected simultaneously in the same detection chamber.

The label is detectable by use of the cartridge's electrodes, and so the label will usually be an electrochemical label, such as a ferrocene. Examples of labels which may be used can be found in WO03/074731, WO2012/085591 and PCT/GB2013/051643. Signal emitted by the label can be detected by a cartridge reader.

The pneumatic portion of the cartridge comprises at least one pneumatic circuit which each control at least one pneumatically controlled valve. The pneumatic portion controls sample flow through the cartridge by the opening and closing of pneumatically controlled valves. The opening and closing of the valves is controlled by changes in pneumatic pressure in the pneumatic circuit that is applied through a pneumatic pressure inlet. Usually, the cartridge contains many pneumatically controlled valves. The pneumatically controlled valves may be controlled by separate pneumatic pressure inlets. These valves can be used to prevent downstream movement of sample through the fluidic portion until necessary steps have been performed and/or to prevent unwanted reverse movement of sample upstream. For example, a valve may be provided upstream of the at least one amplification chamber in order to prevent downstream movement into the at least one amplification chamber until cell lysis and nucleic acid separation has taken place. Following cell lysis and nucleic acid separation the valve upstream of the at least one amplification chamber may be opened in order to allow downstream flow. It can then be closed again, to prevent backflow out of the chamber back towards the sample inlet.

The cartridge comprises at least two electrodes which can provide a potential difference across the at least one detection chamber. The potential difference causes current to flow through the at least one detection chamber, thereby permitting the detection of signal from electrochemically active labels.

Embodiments of the invention will now be described in the context of an exemplary fluid cartridge in which the invention is implemented. Whilst not necessary to understand the present invention, it is beneficial to provide general description of the principles of the structure, manufacture, function and use of the fluidic cartridge and associated methods for performing a test.

The exemplary fluidic cartridge and associated methods chosen to illustrate the present invention are for the detection of *Chlamydia trachomatis* bacterium using PCR amplification and electrochemical detection. However, the skilled person would understand that the invention is not limited to the exemplary fluidic cartridge and associated methods, and is suitable for use in with various different cartridges for a wide variety of sample analysis techniques or biological assays; for example, assays of target nucleic acid sequences in a liquid sample.

Those skilled in the art will understand that the devices and methods of the invention described herein and illustrated in the accompanying drawings are non-limiting exemplary embodiments and that the scope of the present invention is defined solely by the claims. The features illustrated or described in connection with one exemplary embodiment may be combined with features of other embodiments. Such modifications and variations are included within the scope of the present disclosures.

An exemplary cartridge which operates according to the above description will now be described with reference to the accompanying drawings.

1. The Exemplary Cartridge 1.1 Overview

The exemplary cartridge described below is intended to be a single-use, disposable cartridge for performing a test on a sample introduced into the cartridge. The exemplary cartridge is a fluidic cartridge with channels of an appropriate scale (as detailed hereafter). However, the invention may be performed on a microfluidic device, or an LOC. Once the test has been run, it is preferred that the cartridge is disposed of. However, if desired, the cartridge may be sent for re-processing to enable it to be used again.

It is preferred that the cartridge comprises all of the biological agents necessary for conducting the test of choice. For example, the exemplary cartridge is used for detecting the presence, absence or amount of a pathogen of interest. Any pathogen may be detected. Examples of pathogens which may be detected by the cartridge are *Chlamydia trachomatis, Trichomonas vaginalis, Neisseria* gonorrhoea, *Mycoplasma genitalium* and methicillin resistant *Staphylococcus aureus*. To that end the cartridge comprises reagents for nucleic acid amplification. Nucleic acid amplification may be performed using any nucleic acid amplification method. The nucleic acid amplification method may be a thermocycling method in which the temperature at which the method is performed is varied such that different steps of the amplification are able to take place at different temperatures within the cycle. For example melting, annealing of primers and extension may each be performed at different temperatures. By cycling through the temperatures, the timing of each of the steps of the method can be controlled. As an alternative, the nucleic acid amplification may be an isothermal method in which the temperature is kept constant. In both the thermocycling and the isothermal nucleic acid amplification methods, the temperature is controlled during nucleic acid amplification.

Examples of nucleic acid amplification methods are the polymerase chain reaction (PCR), the ligase chain reaction (LCR), strand displacement amplification (SDA), transcription mediated amplification, nucleic acid sequence-based amplification (NASBA), helicase-dependent amplification and loop-mediated isothermal amplification. The reagents for nucleic acid amplification will vary depending of the nucleic acid amplification method used but include a polymerase and nucleotide triphosphates.

As explained below, the cartridge also comprises detection reagents which are capable of detecting the presence or absence of amplified nucleic acids which are the product of the nucleic acid amplification method. The reagents for nucleic acid detection comprise a probe which is capable of hybridising to the amplified nucleic acid. The probe includes a ferrocene label. Following hybridisation of the probe to the amplified nucleic acid, the detection of the nucleic acid occurs via a detectable change in the signal from the label. The change is caused by hydrolysis of the probe, which is achieved using a double strand specific nuclease. The nuclease is a T7 endonuclease. The ferrocene gives different electrochemical signals when it is part of a probe or when it is attached only to a single nucleotide, and so hydrolysis is easily detected. Thus, the change in signal from the label permits detection of the presence of the nucleic acid of interest.

The electrodes allow the detectable change in the signal from the label, which occurs in the presence of the target nucleic acid, to be detected.

The cartridge is configured for use with a cartridge reader (not shown). The cartridge comprises a number of pneumatic, mechanical, thermal and electrical interfaces (described in more detail below) through which the reader interacts with the cartridge to perform the test. Hence, in use, the cartridge would be inserted into the reader, and the reader would be activated to begin interacting with the cartridge via the interfaces to perform the test. For the purposes of understanding the present invention, it is not necessary to describe exactly how the cartridge interacts with the reader to conduct a particular test and provide the test results, but an overview of an exemplary operation of a cartridge is provided hereafter.

1.2 Schematic Diagram of the Exemplary Cartridge

Before explaining the structure and arrangement of the components of an exemplary fluid cartridge in detail, it is helpful to describe the layout of the exemplary cartridge at a high level with reference to the schematic shown in FIG. 1.

It is convenient to consider the overall layout of the cartridge in terms of the flow of liquids, including the liquid sample, through the cartridge. Unless otherwise specified hereafter, the passage of liquids including the liquid sample and the liquid buffers is referred to as the 'fluid pathway' which has an upstream end and a downstream end. Unless otherwise specified hereafter, 'downstream' generally refers to the direction of flow of the liquids and 'upstream' refers to the direction opposite the direction of flow. The fluid pathway in the exemplary cartridge may have different branches (and thus form different fluid pathways), but all pathways have a recognisable direction of flow which permit a skilled person to identify the upstream and downstream directions. However, there is an exception to this general definition, which is when the liquid sample is pumped between the mixing chamber 10 and the bellows 20. In this case, fluid is intermittently pumped back upstream in the opposite direction to its general direction of fluid flow, which is downstream. This mixing serves to mix the lysis and sample and to rehydrate the internal control.

The liquid sample is introduced into the cartridge at a sample mixing chamber 10 through an entry port. A particular arrangement of a preferred entry port may itself form an isolated inventive aspect of the cartridge, as described further in section 3, below. A sample indicator 12 is fluidly coupled to the sample mixing chamber 10 such that a sample introduced into the sample mixing chamber 10 is visible in the sample indicator 12. Also connected to the sample mixing chamber 10 is a blister 14 containing a lysis buffer. The lysis buffer comprises guanidine thiocyanate. Once the sample has been introduced into the sample mixing chamber 10, and a test is started, the lysis blister 14 is collapsed so as to expel the lysis buffer into the sample mixing chamber 10 where it mixes with the liquid sample introduced therein.

Downstream of the sample mixing chamber 10, along a main channel 16, is a coarse filter 18. The coarse filter 18 filters out any large debris in the liquid sample, such as skin or bodily hair, as the liquid sample passes through main channel 16.

Downstream of the coarse filter 18, along the main channel 16, is a bellows 20 having an upstream bellows valve 22a and a downstream bellows valve 22b. As described in more detail below, the bellows 20, together with its upstream and downstream valves 22a-b, is capable of pumping the liquid sample from the upstream end of the fluid pathway (i.e. from the sample mixing chamber 10) to the downstream end. In summary, this is achieved by virtue of flexible membranes within the bellows 20 and the upstream and downstream bellows valves 22a-b which actuate to create local pressure differentials to, on the one hand, draw in the liquid sample from the sample mixing chamber 10 into the bellows 20 and, on the other hand, from the bellows 20 further downstream through the main channel 16. This is achieved by carefully choreographed pneumatic actuation of the flexible membranes in the valves. Particular arrangements of a preferred valve may themselves form isolated inventive aspects of the cartridge, as described further in section 3, below.

Downstream of the bellows along the main channel 16 is a capture column 24. The purpose of the capture column 24 is to separate nucleic acids from cell debris and other cellular components. The capture column comprises a capture filter and a depth filter both made of glass fibres. A particular arrangement of a preferred capture column may itself form an isolated inventive aspect of the cartridge, as described further in section 3, below.

Two branch channels 26, 28 join the main channel 16 between the downstream bellows valve 22b and the capture column 24. The purpose of the branch channels is to introduce liquid buffers necessary for performing the desired test. For example, with the test conducted by the exemplary cartridge, it is necessary to introduce an elution buffer and a wash buffer into the main channel once the sample has passed through. The wash buffer is contained in a wash buffer blister 30 and the elution buffer is contained in an elution buffer blister 32. The introduction of the wash buffer and elution buffer into the main channel 16 is controlled by wash buffer valve 34 and elution buffer valve 36, respectively. At the appropriate point in the test, the wash and elution buffer blisters 30, 32 are collapsed so as to expel the wash and elution buffers into the branch channels 26, 28 and thence into the main channel 16 through the wash and elution buffer valves 34, 36.

Downstream of the capture column 24, along a waste branch 16a of the main channel 16, is a waste chamber 38. A particular arrangement of a preferred waste chamber may itself form an isolated inventive aspect of the cartridge, as described further in section 3, below. The purpose of the waste chamber 38 is to collect the cell debris and cellular components other than nucleic acids and contain them, thereby preventing them from entering the test channel 54a or the control channel 54b. The waste chamber 38 is vented to atmosphere through a waste vent 40, and an aerosol impactor 42 is provided between the waste chamber 38 and the waste vent 40 to prevent particulate matter from escaping from the waste chamber 38 into the atmosphere. A waste chamber valve 44 in the main channel waste branch 16a of the main channel 16 permits and prevents fluids passing into the waste chamber 38 at appropriate points during the test.

Downstream of the capture column 24, along an elution branch 16b of the main channel 16, is an elution chamber 46. The purpose of the elution chamber 46 is to allow the sample preparation to settle and for bubbles to disperse before the sample enters the amplification chambers. An elution chamber valve 48 in the elution branch 16b of the main channel 16 permits and prevents fluids passing into the elution chamber 46 at appropriate points during the test.

Downstream of the elution chamber 46 is a convoluted mixing channel 52. Here the prepared sample is mixed prior to passing through the isolation valve 50.

In the present application, the components upstream of the isolation valve 50 are referred to as being comprised in the 'front end' of the cartridge, whilst the components downstream of the isolation valve 50 are referred to as being comprised in the 'back end' of the cartridge. Broadly speaking, the liquid sample is prepared for analysing in the front end of the cartridge, and the analysis is carried out on the sample in the back end of the cartridge.

The isolation valve 50 is open to permit the prepared liquid sample to pass from the front end to the back end of the cartridge. At an appropriate point in the test, after the liquid sample has been prepared and is within the back end of the cartridge for analysis, the isolation valve 50 is closed to prevent any of the sample from re-entering the front end. Once the isolation valve 50 is closed, it cannot be opened again. The isolation valve 50 also acts as a safeguard in case of a power failure, wherein the reader closes the isolation valve 50 to prevent leakage.

Downstream of the isolation valve 50, the fluid pathway splits into an amplification test channel 54a and an amplification control channel 54b. Each of the amplification channels 54a-b comprises an amplification chamber 56a-b having an amplification chamber inlet valve 58a-b and an amplification chamber outlet valve 60a-b. Any nucleic acid amplification method may be performed in the nucleic acid amplification chamber. If PCR is used, the nucleic acid amplification chambers contain a thermostable DNA polymerase, dNTPs, a pair of primers which are capable of hybridising to the nucleic acid to be amplified. Optionally, the nucleic acid amplification chambers may additionally contain buffer salts, $MgCl_2$, passivation agents, uracil N-glycosylase and dUTP. An example of a thermostable DNA polymerase that may be used is Taq polymerase from *Thermus aquaticus*.

Each of the nucleic acid amplification chambers in the exemplary cartridge comprises reagent containment features in the form of first and second shallow wells formed in the fluidic layer. The reagents to be used in the cartridge are spotted in the wells. In the exemplary cartridge, the test-specific reagents and the generic reagents are isolated from each other by spotting each in a different well. Hence, the test-specific reagents are spotted in a first well in the chamber and the generic reagents are spotted in a second well in the chamber. By spotting the reagents separately, it is easier to swap the test-specific reagents during manufacture for a different set of test-specific reagents, so as to perform a different test, whilst keeping the generic reagents as they are.

In the exemplary cartridge, the ratio of nucleic acid amplification chambers to detection chambers is 1:2. The prepared sample enters the back end of the cartridge at the isolation valve 50 and is split into two nucleic acid amplification chambers. After processing, the each of the two processed measures of sample from the nucleic acid amplification chamber is split into two detection chambers. Therefore, for each sample introduced into the exemplary cartridge, four detection chambers may be filled from two nucleic acid amplification chambers, thus facilitating duplex amplification and 4-plex detection.

However, it will be appreciated that one or three or more nucleic acid amplification chambers may be provided to provide any level of multiplexing desired, and that the number of the detection chambers provided may be adjusted accordingly to maintain a 1:2 ratio of nucleic acid amplification chambers to detection chambers.

The ratio 1:2 is preferred for the exemplary cartridge because such a ratio allows twice the number of target nucleic acids to be assayed compared to the number of different labels required for detection in the detection chambers. However, it will be appreciated that the ratio may be changed depending on the number of labels and PCR targets for the liquid sample. For instance, the ratio may be 1:1, 1:3 or 1:n such that there are n detection chambers branching from the main channel of each fluid pathway when there are n times as many multiplexed PCR targets for the number of labels.

PCR primers specific for *Chlamydia trachomatis* are dried down in the amplification chamber in the amplification test channel together with the other reagents required for nucleic acid amplification. PCR primers specific for a positive control nucleic acid are dried down in the amplification chamber in the amplification control channel together with the other reagents required for nucleic acid amplification. A positive control nucleic acid is also provided in the amplification chamber in the amplification control channel, taken from *Pectobacterium atrosepticum*. The dried down reagents are reconstituted when the liquid sample reaches them.

Downstream of the amplification chamber outlet valves 60a-b each of the amplification channels 54a-b splits into two further detection channels, leading to two detection chambers for each amplification chamber, giving a total of four detection chambers 62a-d in total. The reagents for nucleic acid detection, including the target probe, are dried down in the detection chambers 62a-d downstream of the test amplification chamber 56a or 56b. The reagents for nucleic acid detection including the control probe are dried down in the detection chambers downstream of the control amplification chamber 56a or 56b (whichever is not the test chamber mentioned above). Each detection chamber 62a-d is provided with its own gas spring 64a-d which forms a dead end at the downstream end of the fluid pathway.

Reagents for nucleic acid detection are provided in detection chambers. The reagents for nucleic acid detection include probes having a ferrocene label. These probes are capable of hybridising to the amplified nucleic acids. Following hybridisation of the probes to the amplified nucleic acids, the probes are hydrolysed by a double strand specific nuclease[1] which causes the label to be freed from the rest of the probe. As explained above, freeing of the label from the rest of the probe causes a detectable change in the signal from the label. The control probe is provided in separate detection chambers to the target probe and detection of the target nucleic acid and the control nucleic acid take place in different detection chambers, such that the signals are distinguishable from one another.

Downstream of the amplification outlet valves 60a-b, but upstream of the forks creating the four detection channels, two bypass channels 66a-b respectively join the two amplification channels 54a-b. The purpose of the bypass channels 66a-b is to remove excess liquid sample within the amplification channels 54a-b before the liquid sample enters the detection chambers 62a-d. The bypass channels 66a-b connect to a bypass valve 68, which is also fluidly coupled to the elution chamber branch 16b of the main channel 16, downstream of the isolation valve 50, before the channel splits into amplification channels 54a and 54b.

A particular arrangement of a preferred chamber in the cartridge, such as the first and second amplification chambers or the first to fourth detection chambers, may itself form an isolated inventive aspect of the cartridge, as described further in section 3, below.

It will be appreciated that the number of amplification chambers, and the number of detection chambers in the exemplary cartridge may vary depending on the preferred implementation. Moreover, other configurations of channels, chambers, valves and so on are possible without departing from the scope of the invention, as defined by the claims.

Figure 2:
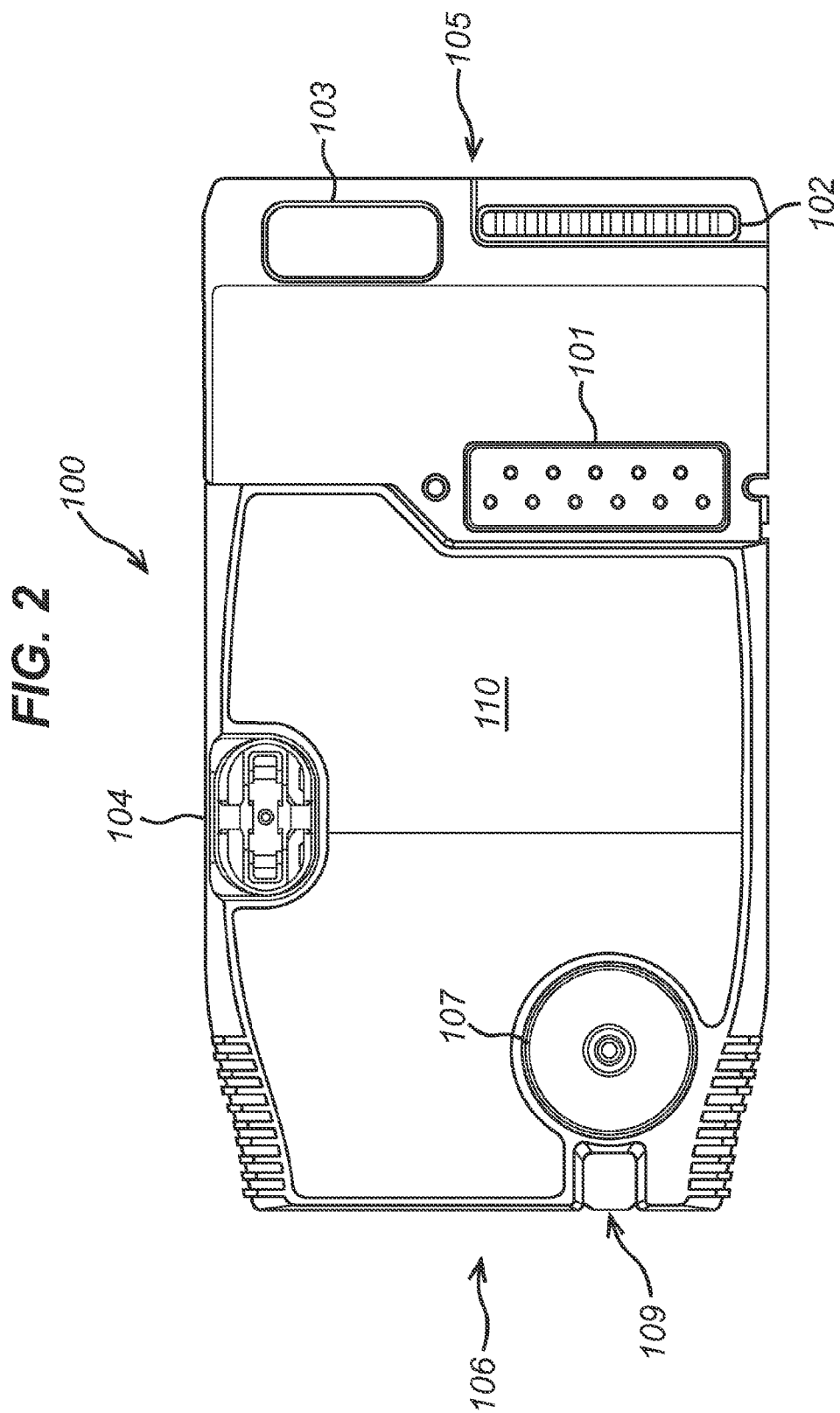
FIG. 2 is a top view of an exemplary fluidic cartridge in which the invention may be provided.

The physical structure and operation of the various components of the exemplary cartridge introduced above will now be explained with reference to FIGS. 2 to 10.
1.3 Physical Structure of an Exemplary Cartridge
1.3.1 Overview and External Features of the Exemplary Cartridge An exemplary cartridge is shown in FIG. 2. As described above, the reader interacts with the cartridge through a plurality of interfaces. The interfaces shown in the exemplary cartridge 100 are: a pneumatic interface 101; an electrical interface 102; a bypass valve interface 103; and an isolation valve interface 104. Each of these interfaces is described in more detail below. It will be appreciated that more or fewer interfaces could be provided, depending on the preferred implementation.

Also provided in the cartridge, but not shown, is a thermal interface. The thermal interface allows the temperature of the amplification chambers to be regulated to allow nucleic acid amplification to take place.

The exemplary cartridge 100 shown in FIG. 2 comprises an insertion end 105 for insertion into the reader, and a non-insertion end 106. Proximate the non-insertion end 106 is a sample inlet 107 for introducing a sample into the sample mixing chamber 10. In the exemplary cartridge, the sample will usually include cells, and the target nucleic acid (if present) can be extracted from these cells, but other fluid samples such as swab eluate, urine, semen, blood, saliva, stool sweat and tears could be used in other implementations. The sample may be introduced into the sample mixing chamber 10 through the sample inlet 107 using a pipette, for example.

The exemplary cartridge 100 and reader are configured such that when the cartridge is inserted into the reader, all of the aforementioned interfaces are actuatable by the reader. On the other hand, the sample inlet 107 remains external to the reader such that a sample may be introduced into the sample mixing chamber 10 whilst the cartridge is inserted into the reader.

The exemplary cartridge 100 shown in FIG. 2 further comprises a sample indicator window 109, through which the sample indicator 12 is visible to determine whether a sample has been introduced into the sample mixing chamber 10.

Figure 3:
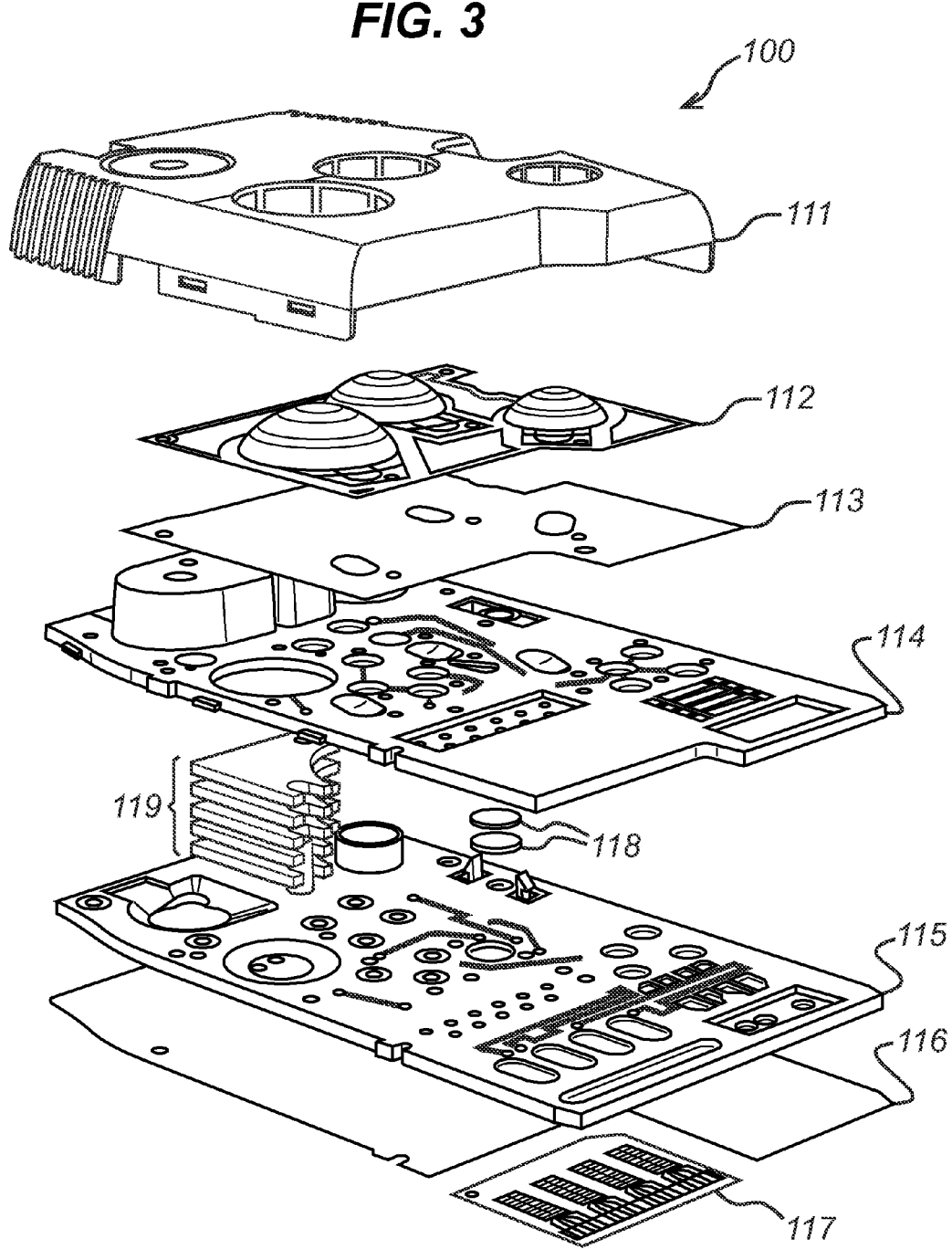
FIG. 3 is an exploded view of the exemplary fluidic cartridge of FIG. 2.

All of the pneumatic, mechanical and electrical interfaces in the exemplary cartridge 100 are located on the same face of the cartridge, in this case the top face 110. The thermal interface (not shown) is provided on the bottom face of the cartridge. This simplifies the design of the reader, which may this provide the associated pneumatic, mechanical and electrical parts which interact with those interfaces in the same region of the reader, thereby making best use of space. It also enables the thermal part of the reader to be provided away from the pneumatic, mechanical and electrical parts.
1.3.2 Internal Components of Cartridge The exemplary cartridge 100 shown in FIG. 2 is formed from various components which shall now be described. FIG. 3 shows an exploded view of the exemplary cartridge 100 of FIG. 2. The cartridge 100 comprises, from top to bottom, a housing 111, a blister sub-assembly 112, a pneumatic foil 113, a pneumatic layer 114, a fluid layer 115 and a fluidic foil 116. Also shown in FIG. 3 is an electrode layer 117, two filters 118 and a plurality of absorbent pads 119, which will be described in more detail below.

The housing 111 is manufactured from acrylonitrile butadiene styrene. The pneumatic and fluidic foils 113, 116 are manufactured from a polyethylene terephthalate/polypropylene composite. The pneumatic and fluidic layers 114, 115 are manufacture from polypropylene.

With the exception of the housing 111, filters 118 and pads 119, each of the components mentioned in the previous paragraph is adhered to its adjacent component or components. Hence, the blister sub-assembly 112 is adhered to the pneumatic foil 113, which is adhered to the pneumatic layer 114, which is adhered to the fluidic layer 115, which is adhered to the fluidic foil 116. The electrode layer 117 is adhered to fluidic layer 115 also.

The adhesion of the layers to each other provides a series of fluid-tight channels in the cartridge, together with associated chambers, valves, pumps, bellows and other components. The channels passing a liquid sample therethrough are liquid-tight and the channels passing a gas therethrough are gas-tight. Optionally, all components are both liquid tight and gas-tight. For example, recesses and openings formed in one or both sides of the pneumatic and fluidic layers create, when sandwiched together and adhered to the pneumatic and fluidic foils, respectively, the shapes necessary to provide the aforesaid channels, chambers, valves, pumps, bellows and other components.

Each of the components referred to above in FIG. 3 will now be described in more detail.

1.3.3 Housing 111

Figure 4:
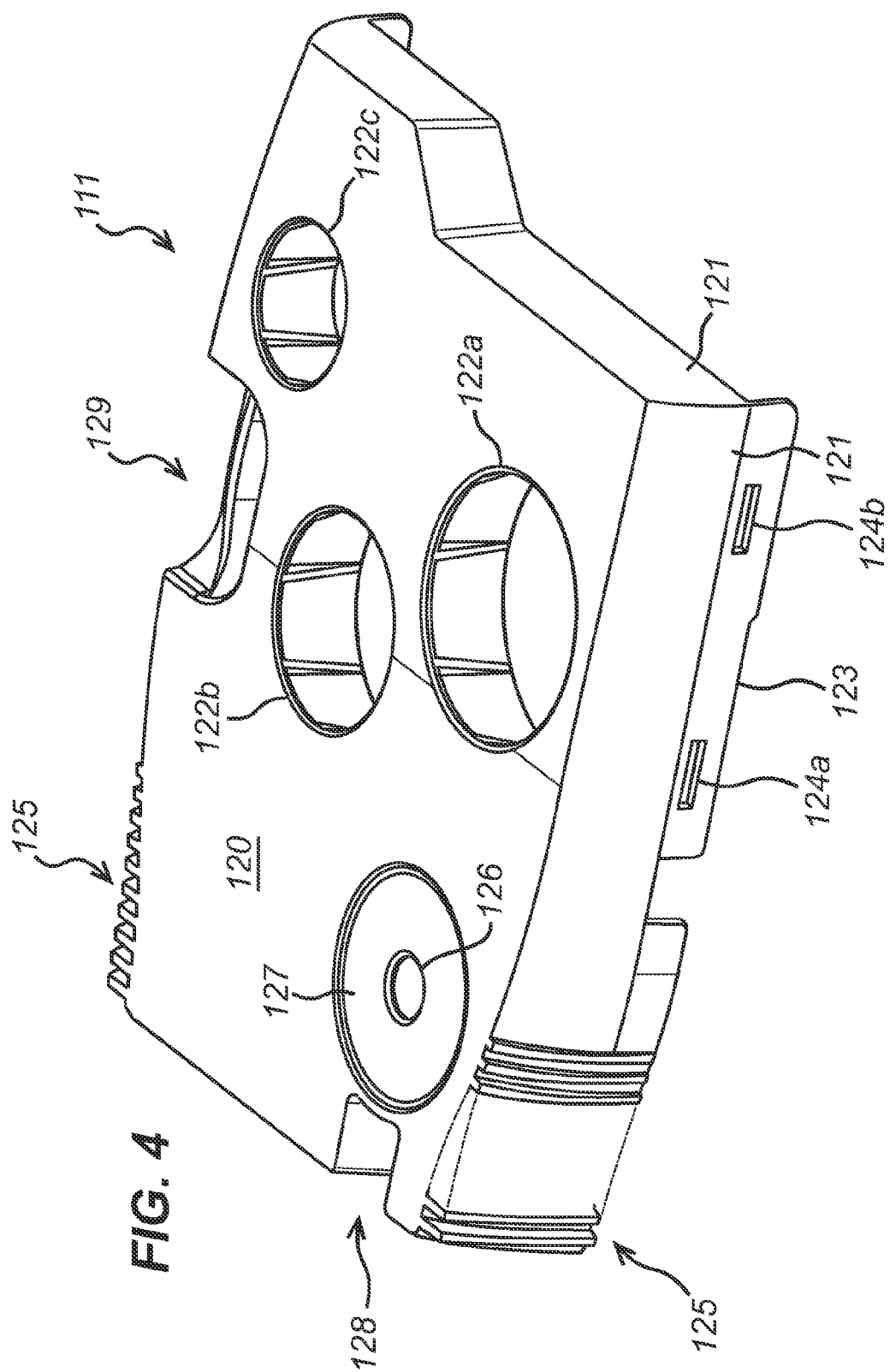
FIG. 4 is a perspective view of the housing of the exemplary fluidic cartridge of FIG. 2.

FIG. 4 shows housing 111 in more detail. As shown, housing 111 comprises a generally rectangular upper surface 120 and walls 121 depending therefrom on all four sides (two of which are visible in FIG. 4). A principal purpose of the housing 111 is to protect certain components of the cartridge, most notably the blister sub-assembly 112 and the isolation valve interface 104. It will therefore be noted that the housing 111 is shorter than the pneumatic and fluidic layers 114, 115 such that it overlies only a portion of those layers when the cartridge 100 is assembled. In the exemplary cartridge 100, the pneumatic interface 101, electronic interface 102, and bypass valve interface 103 are not covered by the housing 111 to provide ease of access by the reader.

The upper surface 120 of the housing 111 has three apertures 122a-c therein, each having walls depending from the peripheries of the apertures to form, when the cartridge is assembled, three recesses. The purpose of the recesses is to house the blisters of the blister sub-assembly 112 such that the blisters may be accessed and pressed by the reader, but are otherwise protected from accidental impact. Naturally, since the exemplary cartridge comprises three blisters, the housing 111 comprises three corresponding apertures 122a-c forming three corresponding recesses. It will be appreciated that more or fewer blisters, apertures and recesses may be provided, depending on the preferred implementation. Alternatively, the housing 111 could comprise a single aperture forming a single recess housing all available blisters.

The side walls 121 of the housing 111 which run along the length of the housing 111 between the insertion end 105 and the non-insertion end 106 of the cartridge 100 comprise flanges 123 along at least a portion of their lower edges. The purpose of the flanges 123 is two-fold. Firstly, they comprise one or more windows 124a-b for receiving a corresponding number of tabs formed in the pneumatic layer 114 to hold the cartridge 100 together. Secondly, the flanges 123 are dimensioned so as to protrude beyond the lower surface of the fluidic foil 116 when the cartridge is assembled, such that the fluidic foil 116 is suspended above a flat surface on which the cartridge 100 is placed. This prevents accidental damage to the fluidic foil 116 which could otherwise result.

Although in the exemplary cartridge depicted in FIG. 4 flanges 123 are provided along substantially the length of two opposing sides of the cartridge, it will be appreciated that flanges may be provided along three or four edges of the cartridge and still suspend the foil above a flat surface on which the cartridge is placed. Similarly, although the cartridge depicted in FIG. 4 shows flanges 123 extending along substantially the entire length of the edge, a flange which extends only partially along an edge may be provided, or multiple flanges may be provided along each edge.

The housing 111 further comprises, at the non-insertion end 106, a grip 125 to facilitate insertion of the cartridge into and removal of the cartridge 100 from the reader by hand. The grip 125 comprises a series of ridges and grooves formed in the housing 111, but alternative structures to increase friction, such as knurls, are also possible.

The housing 111 further comprises a sample inlet aperture 126 through which a sample may be introduced into the sample mixing chamber 10 of the cartridge 100 using a pipette, for example. Surrounding the inlet aperture 126 for a given diameter is a basin 127 recessed into the upper surface 120 of the housing 111 to accommodate a certain amount of spillage of the liquid sample. Whilst the basin 127 of the exemplary embodiment is substantially flat, it may be sloped toward the inlet aperture 126, such that any spillage drains through the inlet aperture 126.

The exemplary housing 111 further comprises a plurality of cut-outs: a first cut-out 128 forming the sample window 109, and a second cut-out 129 to provide access to the isolation valve interface 104. As with the recesses which protect the blisters, by providing access to the isolation valve interface 104 only through a cut-out 129 in the housing 111, the isolation valve interface 104 is protected to some extent from accidental impact, which could actuate the isolation valve and render the cartridge inoperable.

1.3.4 Blister Sub-Assembly 112

Figure 5:
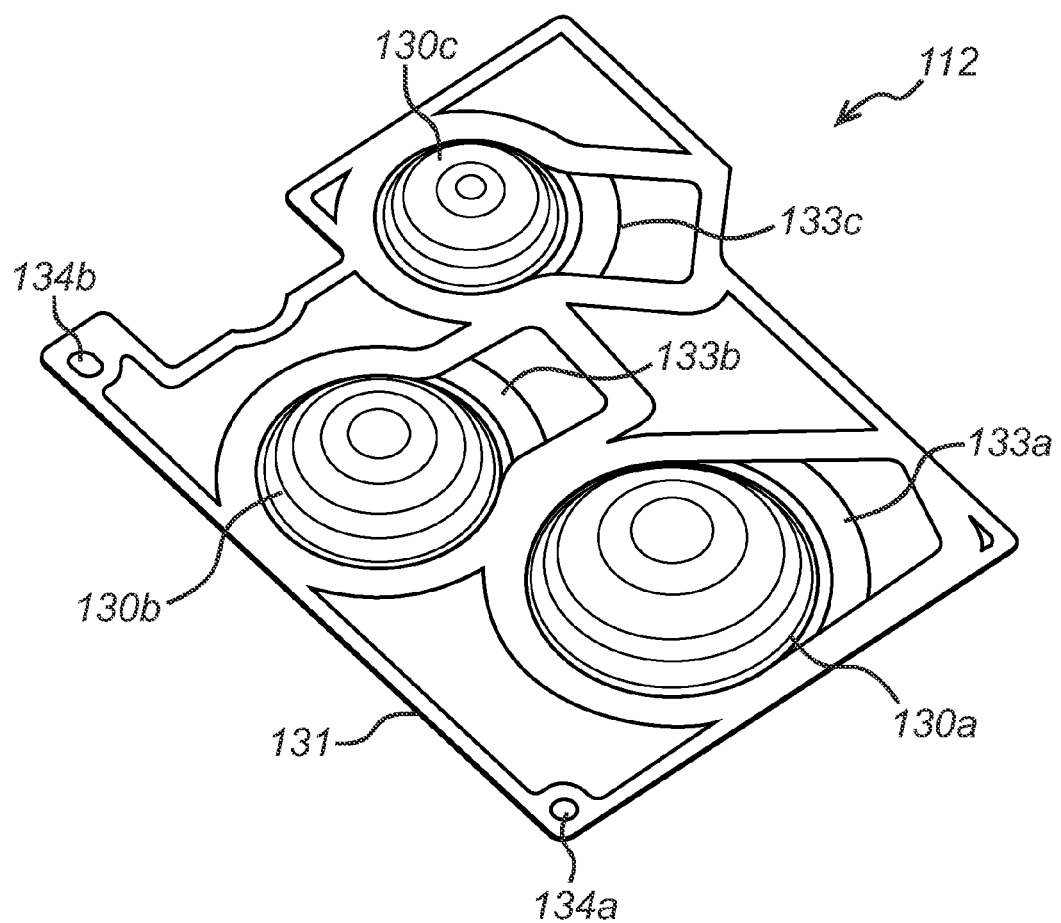
FIG. 5 is a perspective view of the blister sub-assembly of the exemplary fluidic cartridge of FIG. 2.

FIG. 5 shows the blister sub-assembly 112 in more detail. The blister sub-assembly 112 may be manufactured separately, during which the blisters are pre-filled with the liquid reagents necessary for conducting the preferred test, and subsequently adhered to the pneumatic foil 113.

Blister sub-assemblies (or 'blister packs') are familiar to a skilled person. A blister is a collapsible chamber for containing a liquid, which may be expelled from the blister by pressing on the blister and thereby collapsing it. In typical blister packs, the chamber of a blister is sealed by a foil or other frangible layer which ruptures once the pressure inside the chamber reaches a particular magnitude as the blister is collapsed.

In the exemplary cartridge, the blister sub-assembly 112 comprises three blisters 130a-c. These contain, respectively, the lysis buffer which comprises reagents capable of performing cell lysis, the wash buffer and the elution buffer.

The exemplary blister sub-assembly 112 comprises a substrate 131 onto which the aforementioned blisters 130a-c are formed by a deformable polymeric layer which is shaped to provide the chambers. Three apertures 132a-c, corresponding to the three blisters 130a-c, pass through the substrate 132. Each of the apertures is covered by the deformable polymeric layer forming the chamber, which thereby connects the aperture to the chamber but for a seal 133a-c between the respective apertures 132a-c and chambers. Upon application of a suitable pressure on the blister 130a-c, the seal 133a-c breaks, thereby causing the liquid contents of the blister to be ejected from the blister and to flow through the aperture 132a-c in the substrate 131 out of the blister sub-assembly.

As shown, the seals 133a-c at least partially surround the periphery of the chambers, where they meet the substrate 131. At the point in each seal 133a-c which is designed to break (thereby forming the liquid passageway between the aperture 132a-c and chamber), the seal 133a-c may be weaker than the rest of the periphery. This ensures that the correct part of the seal 133a-c breaks when the suitable pressure is applied.

The blisters may be collapsed by the reader when the cartridge is inserted therein. One or more mechanical actuators (such as a foot) may be applied by the reader into the recess so as to collapse the blister.

The blister sub-assembly 112 further comprises two reference holes 134a-b configured to permit an assembly fixture to provide a reference to facilitate positioning of the assembly during manufacture.

1.3.5 Pneumatic Layer 114

Figure 6A:
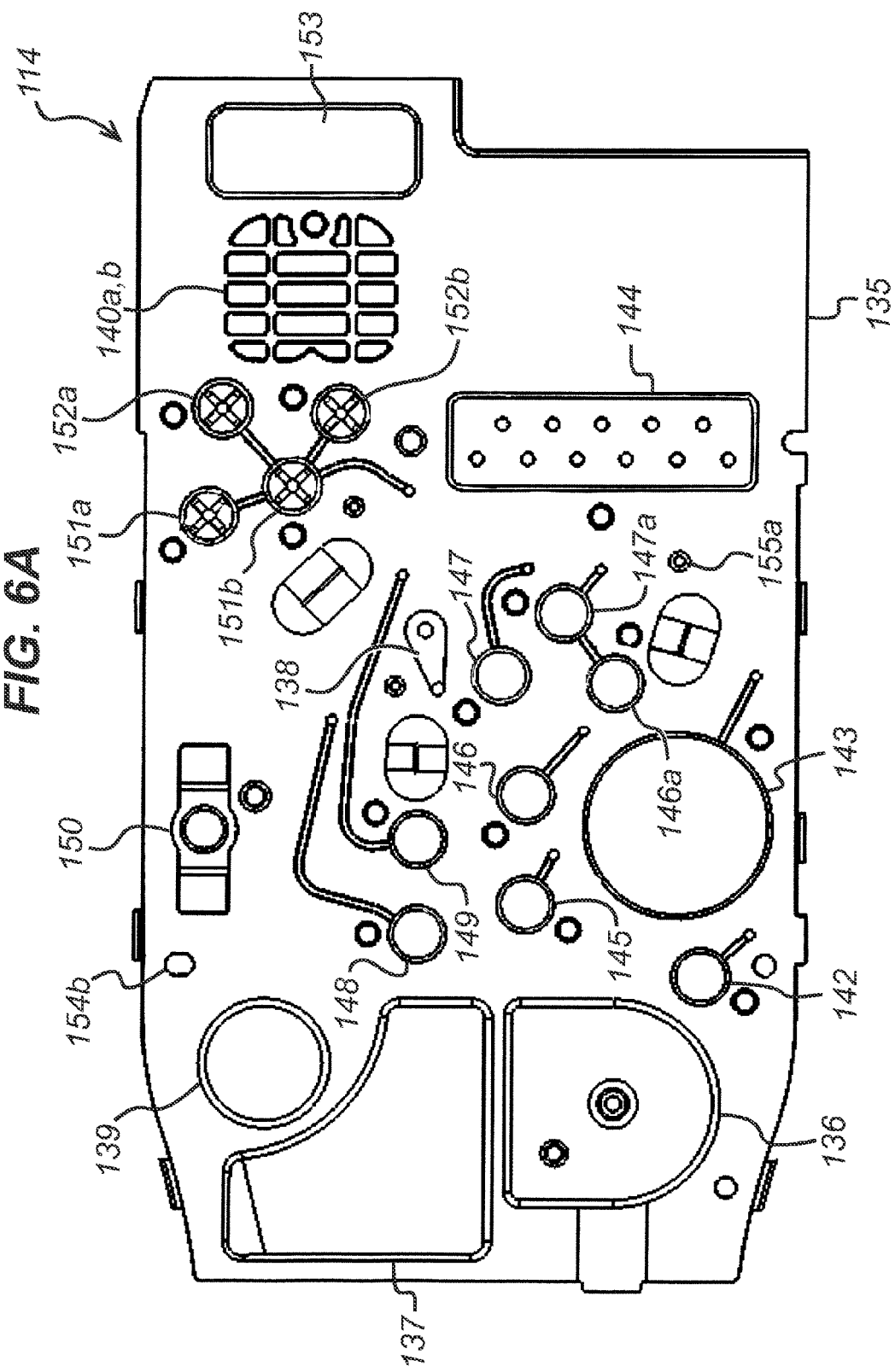
FIG. 6A is a top view of the pneumatic layer of the exemplary fluidic cartridge of FIG. 2.

FIGS. 6A and 6B show the pneumatic layer 114 in more detail. FIG. 6A is a top view of the pneumatic layer and FIG. 6B is a bottom view. The pneumatic layer 114 is comprised of a rigid plastic layer 135 which, in certain places, is overmoulded with a plurality of flexible membranes to form certain components when the cartridge is assembled. The flexible membranes are manufactured from a thermoplastic elastomer.

The rigid plastic layer 135 has a plurality of differently-shaped recesses therein and apertures therethrough. In combination with the fluidic layer 115, certain recesses within, and/or apertures through, the rigid plastic layer 135 form a number of components, including: the sample mixing chamber 136; the waste chamber 137; the capture column 138; the elution chamber 139; the first and second amplification chambers 140a-b; and the first to fourth detection chambers 141a-d. An aperture 142 is also provided to give access to the electrode layer 117.

In combination with the overmoulded flexible membranes and the pneumatic foil 113, certain other apertures through the rigid plastic layer form a number of other components, including: the upstream bellows valve 142; the bellows 143; a pneumatic interface 144; the downstream bellows valve 145; the wash buffer inlet valve 146; the wash buffer air inlet valve 146a; the elution buffer inlet valve 147; the elution buffer air inlet valve 147a; the waste chamber valve 148; the elution chamber valve 149; the isolation valve 150; the first and second amplification chamber inlet valves 151a-b; and first and second amplification chamber outlet valves 152a-b. A further aperture, in combination with an overmoulded flexible membrane (but not the pneumatic foil) forms a bypass valve 153.

With the exception of the isolation valve 150 and the bypass valve 153, the valves formed in the pneumatic layer are pneumatically-operable valves. That is, each valve is operable to open and close a fluidic channel in which the valve is located, and this valve is actuated by applying a particular pressure to a pneumatic control line coupled to the valve. The pneumatic control lines are coupled to the pneumatic interface 144, to which the reader has access when the cartridge 100 is inserted therein. Hence, to actuate a given pneumatic valve, the reader merely applies an appropriate pressure to the pneumatic control line associated with that valve to open or close the valve.

The isolation valve 150 and the bypass valve 153 are also actuated by the reader, but mechanically. Again, each valve is operable to open and close a fluidic channel in which the valve is located, but the valve is actuated by applying one or more mechanical actuators (such as a foot) to the valve.

The pneumatic layer further comprises two reference holes 154a-b configured to permit an assembly fixture to provide a reference to facilitate positioning of the layer during manufacture. When the cartridge is assembled, the reference holes 154a-b in the pneumatic layer align with the reference holes 134a-b in the blister sub-assembly.

The pneumatic layer further comprises apertures 155a-c which, when the cartridge is assembled, line up with apertures 132a-c passing through the substrate 131 of the blister sub-assembly (through the pneumatic foil, as described below).

1.3.6 Pneumatic Foil 113

Figure 7:
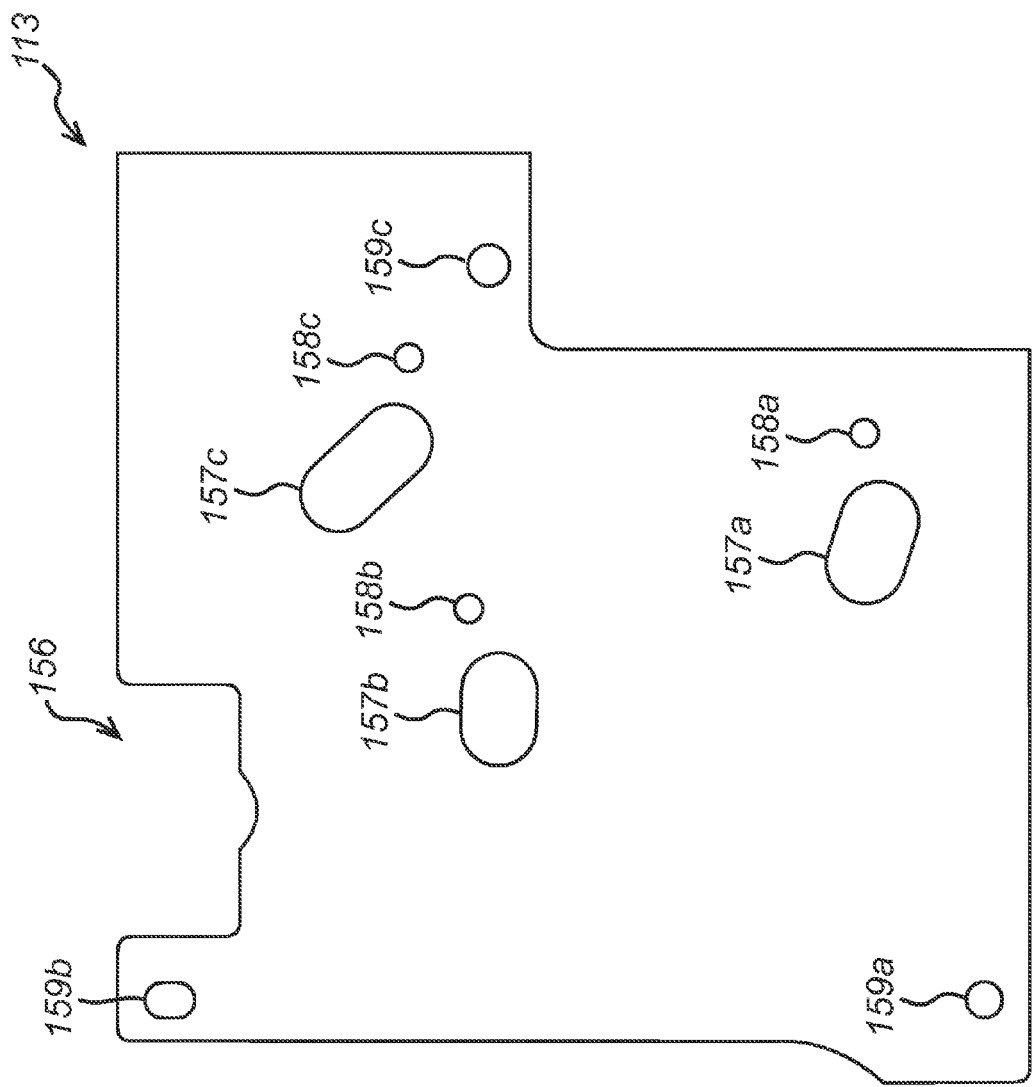
FIG. 7 is a top view of the pneumatic foil of the exemplary fluidic cartridge of FIG. 2.

FIG. 7 shows the pneumatic foil 113 in more detail. As explained above, the pneumatic foil 113 is adhered to the upper surface of the pneumatic layer 114, thereby fluidly sealing channels, chambers, valves, pumps, bellows and other components formed therein. Thus, for the most part, the pneumatic foil 113 is a generally rectangular and planar foil sheet so as to provide an effective seal. Beneficially, the pneumatic foil 113 is inert such that is does not react with the reagents which move through the pneumatic layer 114.

However, the pneumatic foil 113 does not overlie the entire pneumatic layer 114. In particular, the pneumatic foil 113 does not overlie the sample mixing chamber 136 or the waste chamber 137 at the non-insertion end 106 of the cartridge 100, or the bypass valve 153 at the insertion end 105. Moreover, the pneumatic foil 113 comprises cut-outs 156, 157, such that it does not overlie the isolation valve 150 or the pneumatic interface 144, respectively.

The pneumatic foil 113 further comprises three apertures 158a-c which, when the cartridge 100 is assembled, line up with apertures 132a-c passing through the substrate 131 of the blister sub-assembly and 155a-c passing through the pneumatic layer 114. The apertures 158a-c permit the liquid reagents within the blisters to pass to the pneumatic layer 114, and thence to the fluidic layer 115 through apertures 155a-c.

The pneumatic foil 113 comprises two reference holes 159a-b configured to permit an assembly fixture to provide a reference to facilitate positioning of the layer during manufacture. When the cartridge is assembled, the reference holes 159a-b in the pneumatic foil align with the reference holes in the other layers.

The pneumatic foil is a composite foil manufactured from a layer of polyethylene terephthalate, to provide strength, with a layer of polypropylene on top to provide an inert material for contacting the liquid sample and buffers, and also to enable the foil to be heat sealed to the pneumatic layer (also manufactured from polypropylene.

1.3.7 Fluidic Layer 115

Figure 8A:
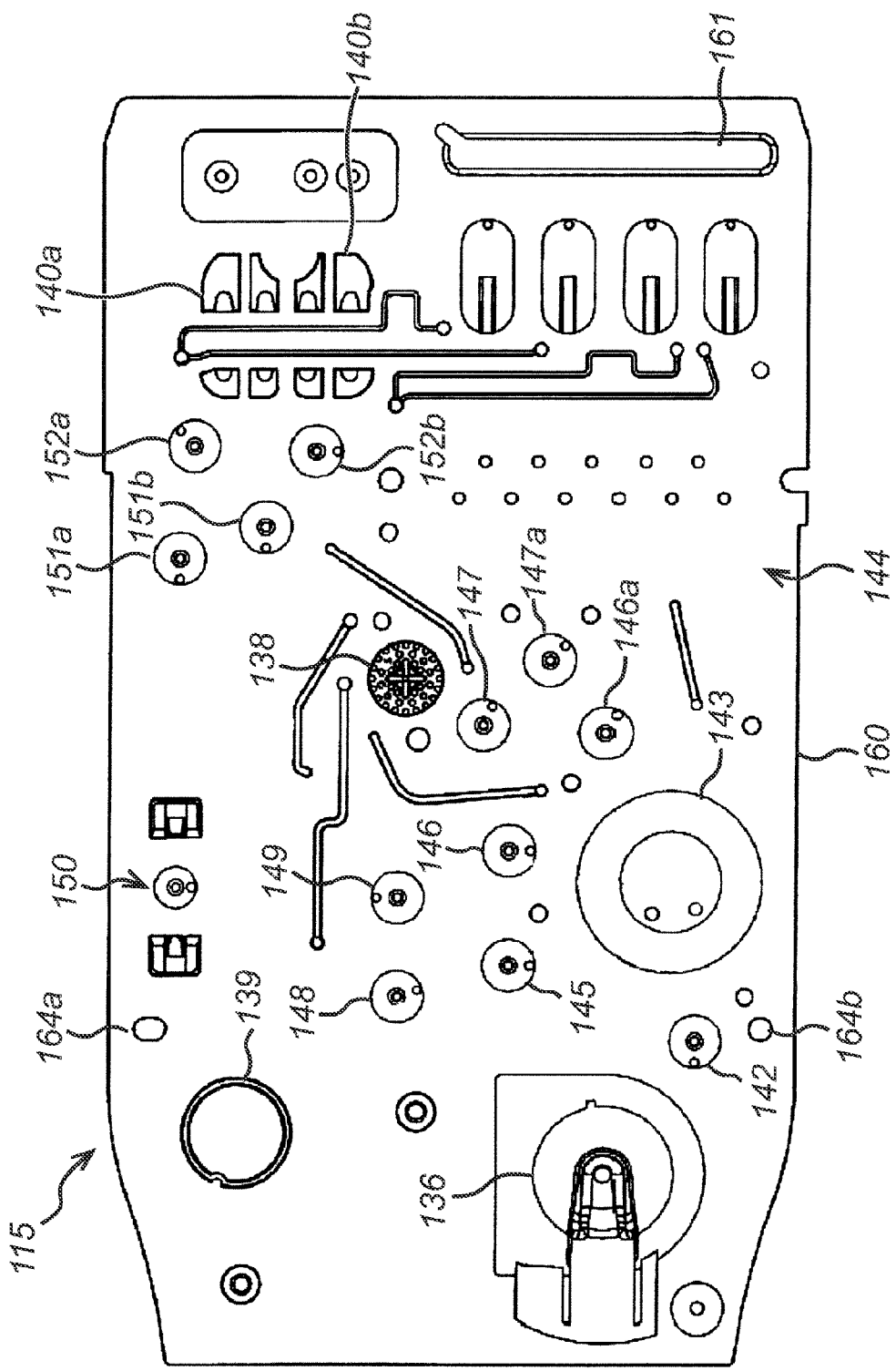
FIG. 8A is a top view of the fluidic layer of the exemplary fluidic cartridge of FIG. 2.
Figure 8B:
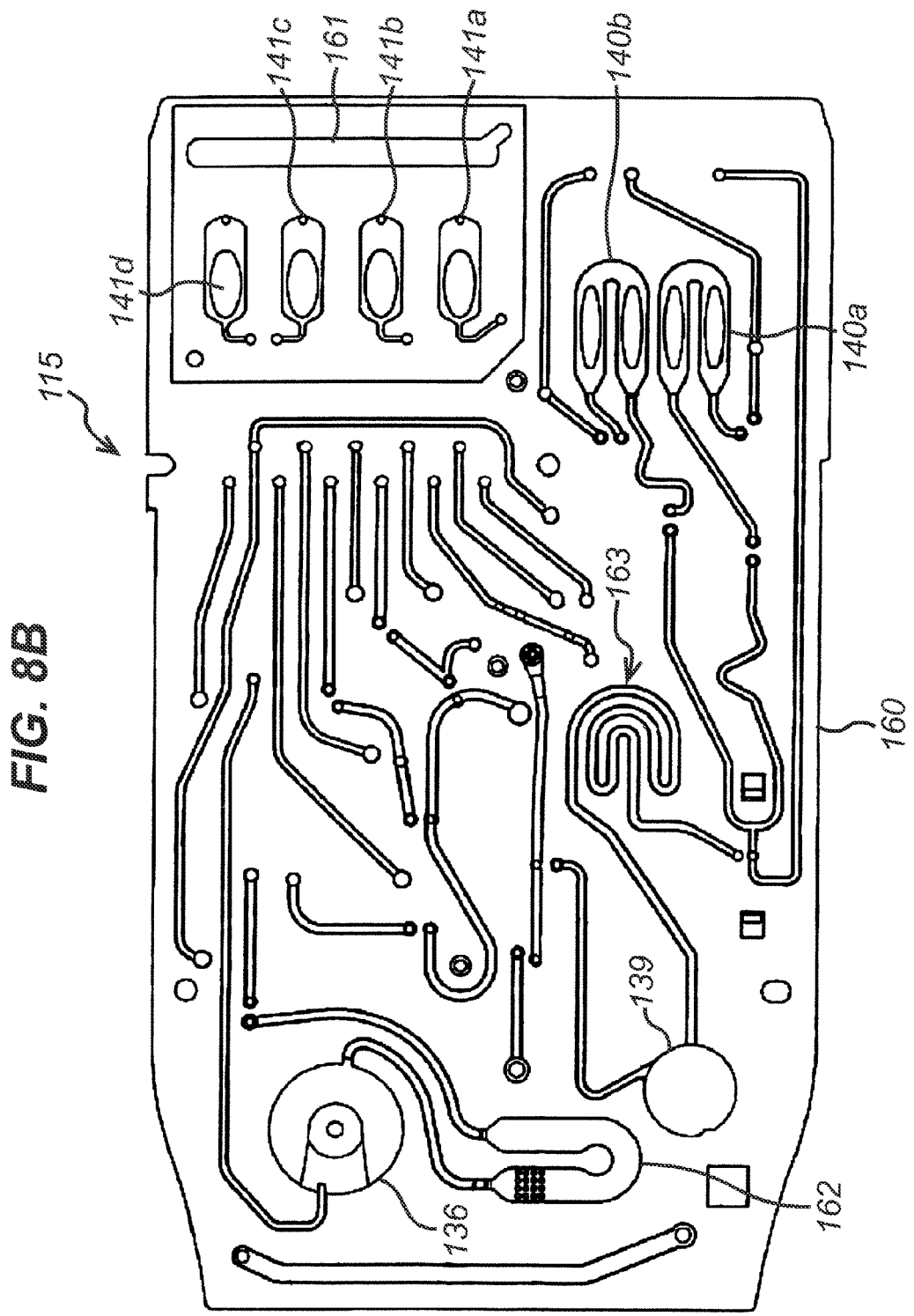
FIG. 8B is a bottom view of the fluidic layer of the exemplary fluidic cartridge of FIG. 2.

FIGS. 8A and 8B show the fluidic layer 115 in more detail. FIG. 8A is a top view of the pneumatic layer and FIG. 8B is a bottom view. The fluidic layer 115 is comprised of a rigid plastic layer 160. As explained previously, the top side of the fluidic layer 115 (not shown) is adhered to the bottom side of the pneumatic layer 113 (see FIG. 5B) such that the various channels, chambers, valves, pumps, bellows and other components formed by a combination of the pneumatic and fluidic layers are aligned.

As with the rigid plastic layer 135 of the pneumatic layer 113, the rigid plastic layer 160 of the fluidic layer 115 has a plurality of differently-shaped recesses therein and apertures therethrough. In combination with the pneumatic layer 113 and the fluidic foil 116, certain recesses within, and/or apertures through, the rigid plastic layer 160 forms certain components, including: the sample inlet chamber 136; the capture column 138; the elution chamber 139; the first and second amplification chambers 140a-b; and the first to fourth detection chambers 141a-d. the upstream bellows valve 142; the bellows 143; the pneumatic interface 144; the downstream bellows valve 145; the wash buffer inlet valve 146; the wash buffer air inlet valve 146a; the elution buffer inlet valve 147; the elution buffer air inlet valve 147a; the waste chamber valve 148; the elution chamber valve 149; the isolation valve 150; the first and second amplification chamber inlet valves 151a-b; and first and second amplification chamber outlet valves 152a-b. An aperture 161 is also provided to give access to the electrode layer 117.

Moreover, in combination with the fluidic foil 116 (but not the pneumatic layer 114), recesses in the fluidic layer 115 also provides the coarse filter 162, the convoluted mixing channel 163, and a plurality of channels which, when the cartridge is assembled, connect the aforementioned components together to enable passage of the liquid sample and liquid reagents through the cartridge, and facilitate pneumatic actuation of the valves, pumps, bellows and other components.

The fluidic layer comprises two reference holes 164a-b configured to permit an assembly fixture to provide a reference to facilitate positioning of the layer during manufacture. When the cartridge is assembled, the reference holes 164a-b in the fluidic layer align with the reference holes in the other layers.

As mentioned above, channels are formed between the pneumatic interface and the various valve and bellows described above. In the exemplary cartridge, the pneumatic interface comprises 11 ports which are connected to the various components as follows.

Port 1: bellows
Port 2: upstream bellows valve
   first and second amplification chamber inlet valves
   first and second amplification chamber outlet valves
Port 3: downstream bellows valve
Port 4: wash buffer inlet valve
Port 5: wash buffer air inlet
Port 6: wash buffer air inlet valve
   elution buffer air inlet valve
Port 7: elution buffer air inlet
Port 8: elution buffer inlet valve
Port 9: reference pressure line
Port 10: elution chamber valve
Port 11: waste chamber valve It will be understood that whilst various inventive aspects of the exemplary cartridge may be implemented using specific ones of the connections listed above (in particular, the first and second amplification chamber inlet and outlet valves being connected to a single port; and the wash and elution buffer air inlets being connected to a single port); the precise configuration listed above is not essential.

1.3.8 Fluidic Foil

Figure 9:
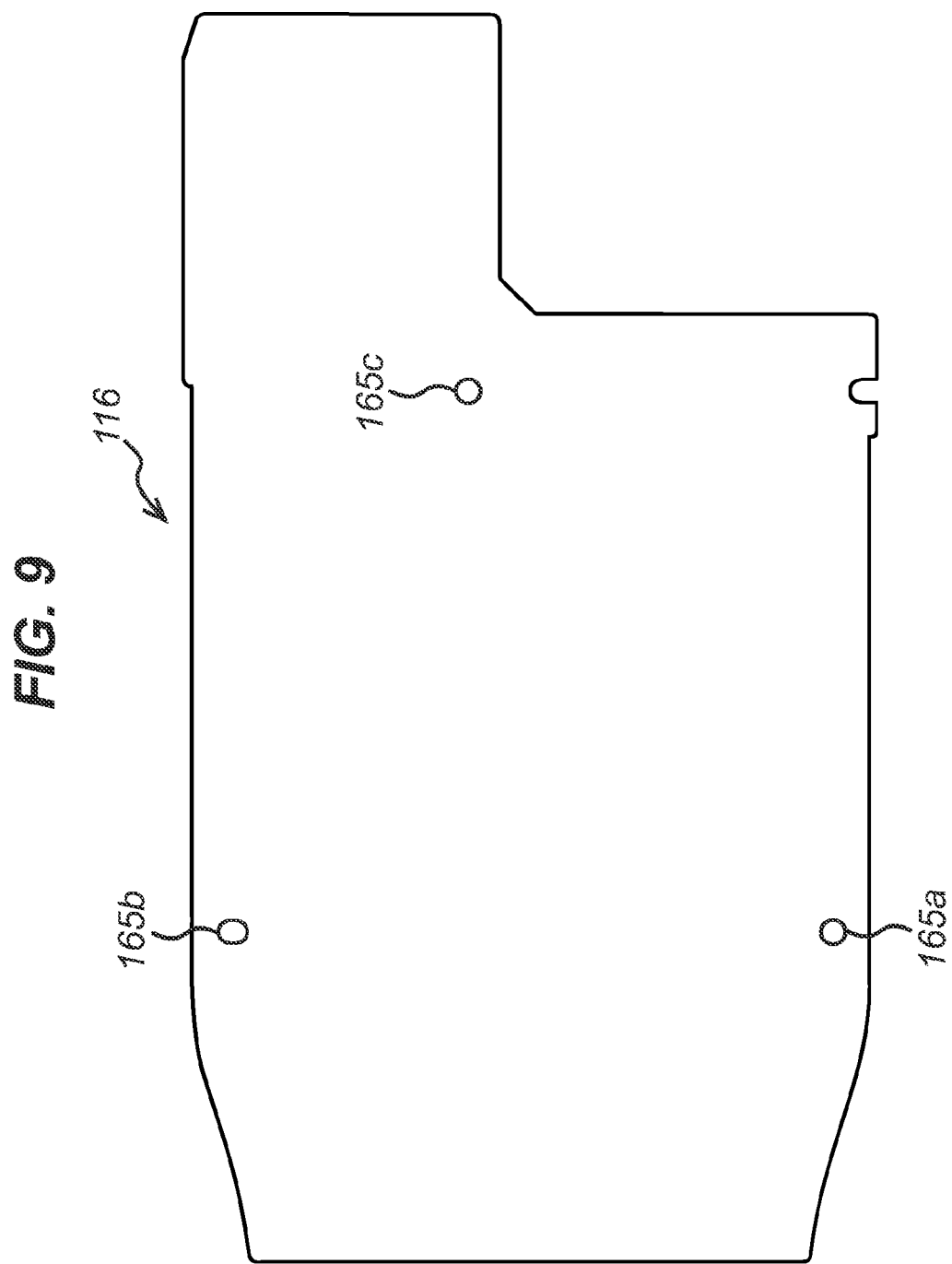
FIG. 9 is a top view of the fluidic foil of the exemplary fluidic cartridge of FIG. 2.

FIG. 9 shows the fluidic foil 116 in more detail. As explained above, the fluidic foil 116 is adhered to the lower surface of the fluidic layer 115, thereby fluidly sealing channels, chambers, valves, pumps, bellows and other components formed therein. Thus, for the most part, the fluidic foil 116 is a generally rectangular and planar foil sheet so as to provide an effective seal. Beneficially, the foil 116 is inert such that is does not react with the reagents which move in the pneumatic layer.

However, the fluidic foil 116 does not overlie the entire fluidic layer 115. In particular, the fluidic foil 116 does not overlie the detection chambers 141a-d at the insertion end 105.

The fluidic foil 116 comprises two reference holes 165a-b configured to permit an assembly fixture to provide a reference to facilitate positioning of the layer during manufacture. When the cartridge is assembled, the reference holes 165a-b in the fluidic foil align with the reference holes in the other layers.

The fluidic foil is a composite foil manufactured from a layer of polyethylene terephthalate, to provide strength, with a layer of polypropylene on top to provide an inert material for contacting the liquid sample and buffers, and also to enable the foil to be heat sealed to the fluidic layer (also manufactured from polypropylene.

1.3.9 Electrode Layer 117

Figure 10:
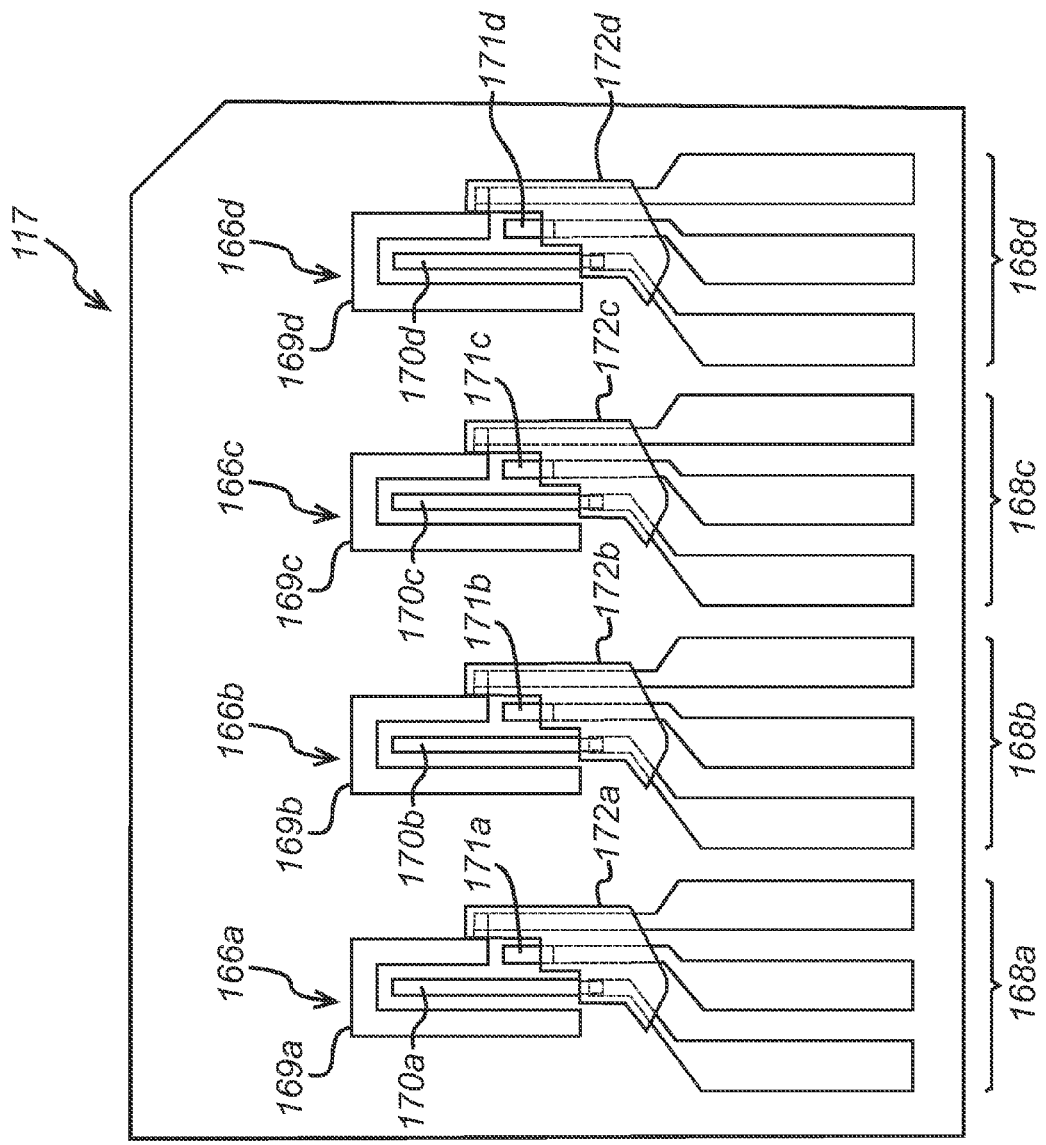
FIG. 10 is a top view of the electrode layer of the exemplary fluidic cartridge of FIG. 2.

Finally, FIG. 10 shows the electrode layer 117 in more detail. As explained above, the electrode layer 117 is adhered to the fluidic layer 115. The electrode layer 117 comprises four sets of detection electrodes 166a-d. Each set of detection electrodes 166a-d comprises first to third electrical contacts 168a-d which couple with corresponding electrical contacts in the reader when the cartridge is inserted therein. Preferably, the electrical contacts are made of silver to optimise the electrical connection. Preferably electrodes which are silver plated with silver chloride are used to ensure a the optimal galvanic behaviour.

Each set of detection electrodes 166a-d comprises a working electrode 169a-d; a counter electrode 170a-d and a reference electrode 171a-d. Each of the electrodes is coupled to a respective electrical contact. Each set of detection electrodes 166a-d also comprises a dielectric 172a-d covering the interface between the electrodes and the respective electrical contacts.

A skilled person understands that electrochemical signalling may be used to indicate the presence of genetic or immuno targets. In the exemplary cartridge this process is performed in the first to fourth detections chambers 141a-d which are optimised to provide the electrochemical test interface.

The electrodes 166a-d are arranged such that a liquid sample within the first to fourth detection chambers 141a-d comes into contact with the first to fourth sets of electrodes 166a-d. In the detection chambers, some compounds in the fluid sample (referred to as the 'electrolyte') have a natural tendency to migrate to electrodes and swap electrons. This galvanic effect is how batteries work.

All combinations of soluble compounds have some electrochemical activity, and the rate at which this activity occurs (i.e. the amount of charge exchanged) is determined by exactly what those compounds are. Hence, it is possible to measure the presence of different analytes in the liquid sample, by searching for characteristic features of their redox electrochemistry.

In the exemplary cartridge, the current required to maintain a given redox state in the detection chambers 141a-d is monitored at different redox states. Current is supplied through the electrolyte from the working electrodes 169a-d to counter electrodes 170a-d.

The reference electrodes 171a-d also contact the electrolyte. Voltages are declared with respect to this reference electrode because its voltage is largely independent of the redox conditions and this therefore means that it is only the redox state of the chemistry at the control electrode that is being measured.

A voltage sweep is applied between the working electrodes 169a-d and counter electrodes 170a-d by the reader, which generates the characteristic range of redox conditions. The current passing between the working electrodes 169a-d and the counter electrodes 170a-d is then measured to obtain the test results. The voltage sweep is a slowly incrementing set of voltages applied between the electrodes. Preferably the sweep is from about −0.7 volts to about +1 volts relative to the reference electrode. The voltage is applied in consecutive incrementing pulses having a pulse modulation amplitude of between 30 and 80 millivolts (preferably between 40 and 60 millivolts; more preferably 50 millivolts). Preferably the step increment from one pulse to the next is between 1 and 5 millivolts (preferably between 2 and 4 millivolts; more preferably 3 millivolts). By applying these voltages across the electrodes, current measurements in the scale of 100s of nano amps may be obtained.

The particular arrangement of detection electrodes illustrated in FIG. 10 may itself form an isolated inventive aspect of the cartridge. Conventionally, the counter electrode in a potentiostat is larger than the working electrode to provide an ample supply of surplus electrons. However, it has been found that reversing this convention surprisingly offers better results for the exemplary cartridge. For the electrochemistry performed on the liquid sample described above in the exemplary cartridge, it is found that having a working electrode which is larger than the counter electrode provides larger signals and improved results by way of increased sensitivity. In other words, having a current flow from a relatively large working electrode to a relatively small counter electrode offers improvements over the conventional arrangement.

Preferably each working electrodes 169a-d is formed in a U-shape and each counter electrode 170a-d is formed in a straight elongate shape between the two prongs of the respective U-shaped working electrode.

The method operation of the exemplary cartridge introduced above will now be briefly explained.

1.4 Method of Operation of the Exemplary Cartridge 1.4.1 The Front End

As described above, a fluid sample (such as a urine sample) is introduced into the sample mixing chamber 10 using a pipette. A portion of the sample passes to the sample indicator 12 to show that a sample is present in the sample mixing chamber.

Once the cartridge 100 with a sample in the mixing chamber 10 is inserted into a reader, and the reader is activated, the test may commence. Firstly, the reader will apply a mechanical actuator (such as a foot) to collapse the lysis buffer blister 14. In doing so, the lysis buffer will be expelled into the sample mixing chamber 10 where it will mix with the sample.

The bellows 20 and its valves 22a-b then moves the liquid sample and lysis buffer back and forth into the sample mixing chamber 10 so as to mix the lysis and sample and to rehydrate the internal control. Following the mixing step, incubation of the sample and lysis buffer occurs to allow cell lysis to take place.

The bellows 20 and its valves 22a-b will then commence operation to pump the sample from the sample mixing chamber 10, into the main channel 16, through the coarse filter 18 and toward the capture column 24. Within the capture column 24 nucleic acids are specifically bound to a filter in the capture column on the basis of their size and charge. The unwanted liquid sample passes through to the waste chamber 38.

Once the unwanted liquid sample has passed to the waste chamber 38, leaving the nucleic acids bound to the capture column 24, the reader applies a mechanical actuator (such as a foot) to collapse the wash buffer blister 30. In doing so, the wash buffer will be expelled into the first branch channel 26, and thence into the main channel 16. Again, the bellows 20 and its valves 22a-b will commence operation to pump the wash buffer through the main channel 16 and through the capture column 24 to wash any remaining unwanted cell debris and other cellular components out of the capture column with the wash buffer through to the waste chamber 38, or else the wash buffer will be flushed into the waste chambers using air from the wash and/or elution buffer air inlets.

Once the wash sample has passed to the waste chamber 38, leaving only the bound and purified nucleic acids in the capture column 24, the reader applies a mechanical actuator (such as a foot) to collapse the elution buffer blister 32. In doing so, the elution buffer will be expelled into the second branch channel 28, and thence into the main channel 16. Again, the bellows 20 and its valves 22a-b will commence operation to pump the elution buffer through the main channel 16 and through the capture column 24 to elute the nucleic acids from the capture column, or else the elution buffer will be flushed into the capture column using air from the wash and/or elution buffer air inlets. The prepared liquid sample then passes through to the elution chamber 46; again, either by being pumped or flushed as described above.

The sample settles in the elution chamber 46 allowing bubbles to disperse before entering the amplification chambers.

1.4.2 The Back End

The bellows 20 and its valves 22a-b will then commence operation to pump the liquid sample from the elution chamber 46, through the isolation valve 59, through the mixing channel 52 and into the amplification chambers 56a-b, or else the sample will be flushed into the amplification chambers using air from the wash and/or elution buffer air inlets. In the nucleic acid amplification chambers 56a-d the nucleic acid of interest, if present, is amplified such that it is present at a detectable level. The control nucleic acid is also amplified such that it is present at a detectable level. As mentioned above, any nucleic acid amplification method may be used. Where PCR is used, primers specifically hybridise to the nucleic acid of interest and are extended by a thermostable polymerase such as Taq polymerase via the addition of dNTPs to the 3' end of each of the primers. Any excess liquid sample may be removed from the fluid pathway through the bypass channels 68.

The bellows 20 and its valves 22a-b will then commence operation to pump the liquid sample from the amplification chambers 56a-b and into the detection chambers 62a-d, or else the sample will be flushed into the detection chambers using air from the wash and/or elution buffer air inlets. In the detection chambers, the target probe specifically hybridises to the target amplified nucleic acid of interest and the control probe specifically hybridises to the amplified control nucleic acid. The nuclease hydrolyses the target and control probes following hybridisation of the probes to the amplified nucleic acid. The hydrolysis of the target and control probes frees the labels from the probes causing a detectable change in the signal from the labels to occur.

Once the liquid sample occupies the detection chambers, the reader applies a mechanical actuator to the isolation valve 50 to close the valve and isolate the liquid sample in the back end of the device.

The electrodes provide a potential difference across the at least one detection chamber. Depending on the state of the label (i.e. whether it is attached to the full length probe or the probe has been hydrolysed and it is free or attached to a single nucleotide or short part of the probe), the current that is able to flow through the detection chamber will differ. The electrodes therefore allow detection by the reader of the change in the signal from the label which results from hydrolysis of hybridised probe.

2. Additional Isolated Inventive Aspects

The following is a non-exhaustive list of isolated aspects of the exemplary cartridge described above which may be claimed. These aspects are described with reference to FIGS. 11 to 15. The inclusion of this section does not preclude there being further aspects of the exemplary cartridge described above which may also be claimed.

2.1 Valves for Minimising Dead Volume

An advantageous arrangement for a valve in a fluidic cartridge will now be described, which may form an isolated inventive aspect.

Hence, in one aspect, there is provided a valve for a fluidic cartridge, the valve comprising:
  a valve cavity having first and second openings connected to first and second passageways, respectively; and
  a flexible membrane movable between a closed position, in which the flexible membrane seals against the first and second openings to prevent fluid flow between the first and second passageways, and an open position, in which the flexible membrane is spaced apart from the first and second openings to permit fluid to flow between the first and second passageways;

wherein the a valve cavity comprises a roof and a floor, the floor comprising said first and second openings; and further comprising:

an abutment between the flexible membrane and the roof of the valve cavity, such that the abutment restricts movement of the membrane in its open position.

Preferably the abutment is provided on the flexible membrane, and comprises one or more of a protrusion, a cage, a lip or a cross structure.

It is sometimes advantageous to limit the extent to which the flexible membrane in a valve described herein is able to travel in its open position. That is, it is desirable to minimise the distance which the valve membrane moves to its open, and thus minimise the distance it must travel to close. By minimising this distance, the dead volume within the valve cavity is reduced, improving the reactivity of the valve.

Figure 11:
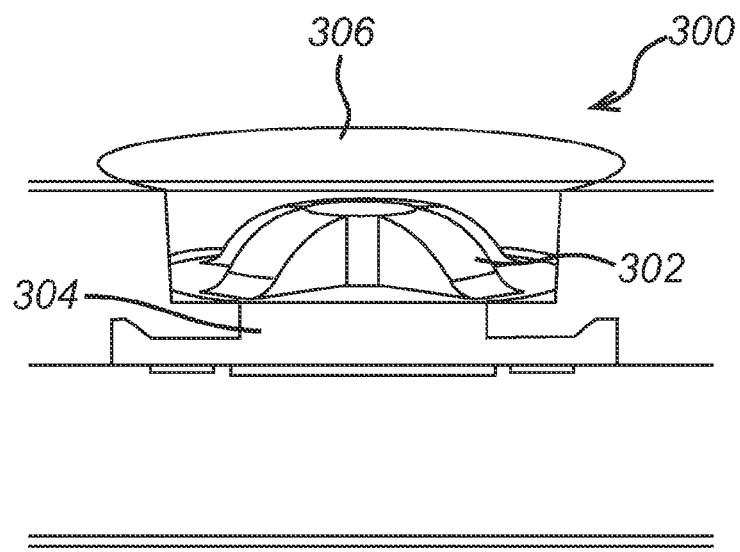
FIG. 11 is a section view of an advantageous valve arrangement which may form an isolated inventive aspect.

Hence, as shown in more detail in FIG. 11, preferred embodiments of a valve 300 further comprise an abutment 302. The abutment of the illustrated example is a cross structure, but in different embodiments may be a protrusion, cage, lip or similar, attached to the upper surface of the flexible membrane 304 so as to contact the roof 306 of the valve cavity and thus limit movement of the membrane in its open position.

It should be appreciated that the channels and openings of the valve are not shown in FIG. 11.

The abutment is particularly advantageous when filing the amplification chambers of the exemplary cartridge, because it reduces the dead-volume in the valve cavity and thus limits the distance between the bottom surface of the flexible membrane and the openings in the valve cavity, thereby permitting a more precise volume of fluid to be metered into the amplification chambers.

2.2 Crack Pressure in Valves

An advantageous arrangement for a valve in a fluidic cartridge will now be described, which may form an isolated inventive aspect.

Hence, in one aspect, there is provided a valve for a fluidic cartridge, the valve comprising:

a valve cavity having first and second openings connected to first and second passageways, respectively;

a flexible membrane within the valve cavity movable between a closed position, in which the flexible membrane seals against the first and second openings to prevent fluid flow between the first and second passageways, and an open position, in which the flexible membrane is spaced apart from the first and second openings to permit fluid to flow between the first and second passageways; wherein the valve is configured such that a pressure required in the first passageway to move the flexible membrane from the closed position to the open position is higher than a pressure required in the second passageway to move the flexible membrane from the closed position to the open position.

It will be appreciated that within the valve cavity there is a portion (known as the valve chamber) between the flexible membrane and the floor. There is also a portion within the valve cavity on the other side of the flexible membrane to the valve chamber. This portion will have a volume. The pressure within that volume may be changed by applying a positive or gauge pressure to the volume via an actuation channel, for example. The actuation channel may be connected to a source of positive or gauge pressure via a pneumatic interface, for example. The pressure within the volume is known as the actuation pressure. This operation is described in more detail above.

In a preferred arrangement, the first and second openings may be arranged such that fluid in the first passageway acts on the flexible membrane only over a relatively small cross-sectional area whereas fluid in the second passageway acts on the flexible membrane over a larger cross-sectional area, preferably substantially the whole membrane.

The effect of this is that the valve is able to withstand a much greater pressure in the first passageway that in the second passageway.

Preferably the valve cavity has a floor comprising the first and second openings and one or more walls between which the flexible membrane extends; and wherein the second opening is coupled to a recess in the floor between the opening and the flexible membrane, the recess having a larger cross-sectional area than the opening.

Preferably the first opening is located centrally within the floor and the recess extends around the first opening, such that the second opening is located between the first opening and a wall of the valve cavity. In a particularly preferred arrangement, the valve cavity has a circular cross section, and the recess is an annular recess which surrounds the first opening.

Preferably the opening of the second fluid passageway is located adjacent the perimeter of the valve chamber. Preferably the valve chamber has a diameter of between 2 and 10 mm, preferably between 3 and 7 mm and more preferably 4 and 6 mm. More preferably, the second opening is offset by 2 mm from the first opening.

Figure 12:
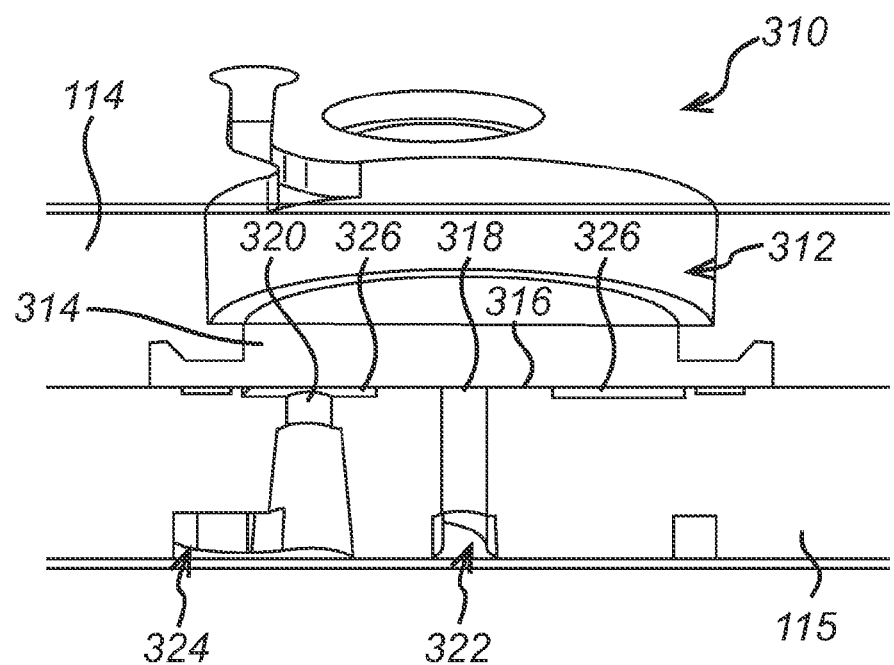
FIG. 12 is a section view of another advantageous valve arrangement which may form an isolated inventive aspect.
Figure 13A:
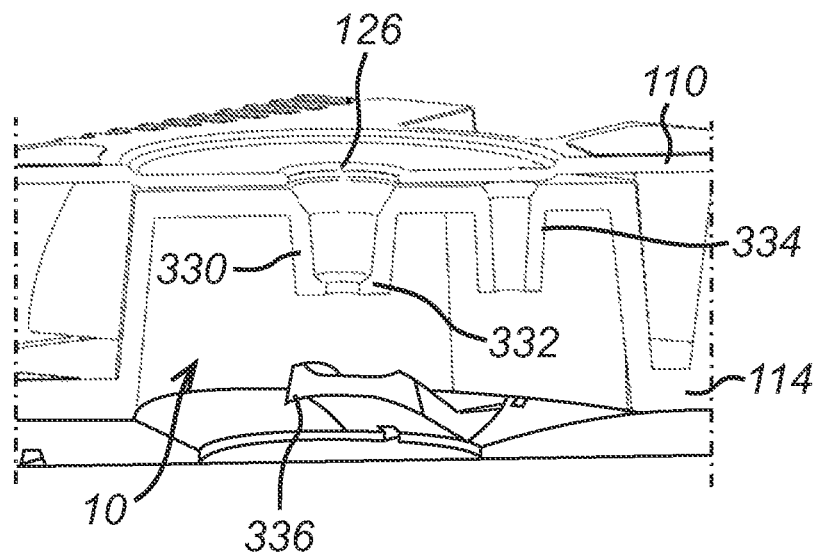
FIG. 13a is a section view of an advantageous inlet port arrangement which may form an isolated inventive aspect.
Figure 13B:
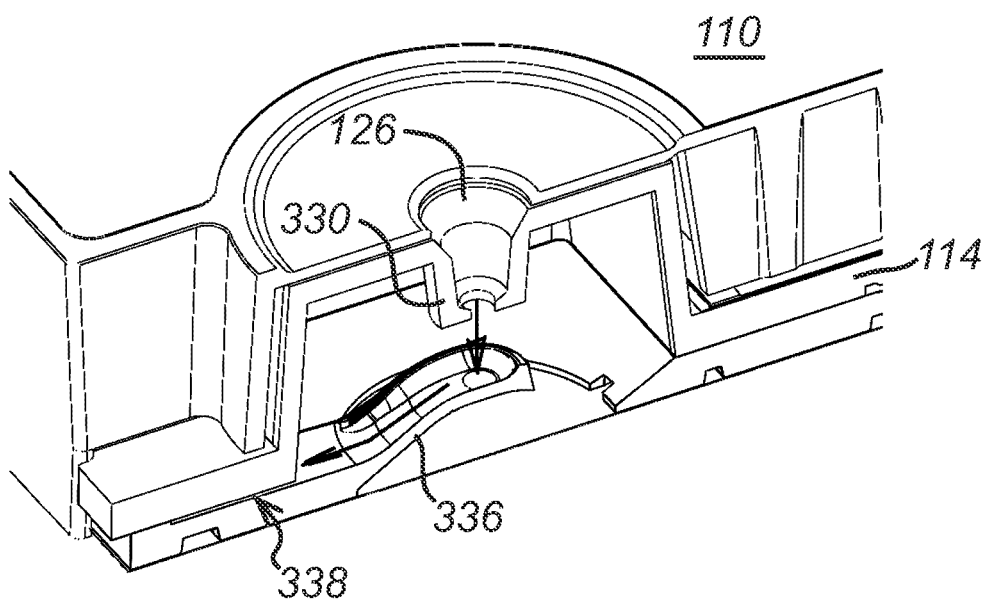

An exemplary valve is shown in FIG. 12 in its closed position. The valve 310 may be used in place of any of the valves of the exemplary fluidic cartridge shown above. The valve comprises a valve cavity 312 having a flexible membrane 314 overlying a cavity floor 316 in which first 318 and second 320 apertures are provided, leading to first 322 and second 324 fluid passageways, respectively.

The cavity 312 is formed from a void in a first polymer layer (preferably the fluidic layer 114 of the exemplary cartridge) together with a second polymer layer (preferably the second fluidic layer 115 of the exemplary cartridge).

The flexible membrane 314 is shown lying across the floor 316 of the cavity such that the valve is shown in its closed position. The valve is movable from this position to an open position (where it is spaced from the floor 316 and the apertures 322, 324 to form a valve chamber), as described herein.

The first opening 318 of the valve is centrally located within the perimeter of the void formed in the first polymer layer, and is therefore centrally located in the valve cavity 312. The second opening 324 of the valve is offset from the first opening 322. The second opening is coupled to an annular recess 326 in the floor, and thus the cross-sectional area over which the fluid in the second passageway 324 acts on the flexible membrane 314 is much larger than the cross-sectional area over which the fluid in the first passageway 322 acts on the flexible membrane.

The pressure of a fluid in the first passageway acts on the flexible membrane only over a relatively small cross-sectional area of the flexible membrane. Thus, because the pressure of a fluid in the valve cavity on the other side of the flexible membrane acts over the whole membrane, it may be lower without allowing the membrane to move to its open position.

In contrast, the pressure of a fluid in the second passageway acts on the flexible membrane over a relatively large cross-sectional area of the flexible membrane. Since the respective cross-sectional areas are closer, so too is the pressure in the second passageway which the flexible membrane is able to withstand vis-à-vis the pressure in the valve cavity.

Preferably, the respective cross-sectional areas of the openings of the fluid passageways allows the membrane to resist pressures around 2.5 times the actuation pressure on the first, central, fluid passageway, but only pressures equal to the actuation pressure (i.e. the pressure in the valve cavity) on the opening of the second, offset, fluid passageway.

2.3 Entry Port Design

An advantageous arrangement for an entry port on a fluidic cartridge will now be described, which may form an isolated inventive aspect.

Hence, in one aspect, there is provided a fluidic cartridge for processing a liquid sample, the cartridge having a sample mixing chamber comprising:
   a sample inlet aperture for introducing a liquid sample into the sample mixing chamber;
   a cage surrounding the inlet aperture and extending into the sample mixing chamber, the cage further comprising one or more protrusions extending radially inwardly to abut against a sample delivery device introduced through the sample inlet.

The body of the cage may be formed from one or more elongate bars, or one or more solid walls, depending from the roof of the sample mixing chamber. If solid walls are provided, there is preferably an aperture in the lower portion of the walls through which a liquid sample introduced by the sample delivery device can pass. Preferably the bars or wall forming the body are tapered to conform to the nib of a conventional sample delivery device introduced through the sample inlet.

Solid walls have the additional advantage that they provide a barrier to prevent fluid introduced into the mixing chamber from escaping out of the inlet aperture, which is particularly useful if the cartridge is turned upside-down during use.

If the cage is formed from solid walls, the protrusion may be a ledge extending inwardly from the walls leaving an aperture. Preferably the protrusion extending from the sides of the inlet aperture is positioned above the floor of the sample mixing chamber; more preferably above a liquid fill level of the sample mixing chamber. This prevents liquid sample from being sucked back into the sample delivery device once introduced into the mixing chamber.

Preferably a vent is provided in the sample mixing chamber to allow air to escape from the chamber during the introduction of the sample. This is particularly useful when the inlet aperture is sealed by the sample delivery device.

Preferably a guide channel is provided within the sample mixing chamber (a portion of which is preferably directly underneath the inlet aperture) to direct the sample introduced by a sample delivery device into a visual indicator region. An exemplary visual indicator region is described above in connection with the exemplary cartridge.

Preferably a change in refractive index of the visual indicator region described herein identifies when a sample has been introduced. The visual indicator region may comprise a narrow fluid passageway, which becomes filled by the fluid sample via capillary action. The filling of the narrow fluid passageway changes the refractive index of the visual indicator region and a colour change identifies when a sample has been introduced.

A preferred embodiment of this aspect will now be described with reference to the exemplary fluidic cartridge. The housing 111 (see FIG. 4) comprises a sample inlet aperture 126 through which a sample may be introduced into the sample mixing chamber 10 of the cartridge 100 using a pipette, for example. As shown in more detail in FIG. 13a, the sample mixing chamber 10 is formed from the pneumatic layer 114, which has a roof adjacent the housing 111 in the region of the inlet aperture, and a corresponding inlet aperture through which a sample may be introduced into the sample mixing chamber 10.

The roof of the mixing chamber 10 comprises a cage structure formed by walls 330 surrounding the inlet aperture 126 which extend into the sample mixing chamber 10 from the roof, and a ledge 332 extending radially inwardly from the walls 330. The shape of the cage structure allows a sample delivery device, such as a pipette, to be located in the correct position in the sample mixing chamber 10, and the ledge 332 prevents the pipette contacting the surfaces of the sample mixing chamber 10, thereby reducing the risk of contamination. The walls 330 can be tapered to further increase the engagement with the pipette.

Once the sample delivery device is located through the aperture, the user can dispense the sample. The ledge 332 is positioned above a nominal liquid fill level (not shown) of the sample mixing chamber so as to prevent the user from accidentally sucking the sample back up after dispensing it into the chamber.

A vent 334 into the chamber is provided to allow air to escape in the event that the inlet aperture is sealed by the sample delivery device.

A guide 336 is provided within the sample mixing chamber 10, a portion of which is directly underneath the inlet aperture 126 to direct the sample introduced by a sample delivery device into a visual indicator region 338. An exemplary visual indicator region is described above in connection with the exemplary cartridge.

2.4 Thermal Isolation Pockets

An advantageous arrangement for thermal isolation pockets for a nucleic acid amplification chamber on a fluidic cartridge will now be described, which may form an isolated inventive aspect.

In nucleic acid amplification and detection, it is preferable to apply heat evenly throughout the liquid sample. Whilst it is possible to do this without difficulty in a laboratory by placing heat sources equidistantly around the sample, it is much harder to achieve in a cartridge.

Hence, in one aspect, there is provided a fluidic cartridge for performing nucleic acid amplification on a liquid sample, the cartridge comprising at least one sample processing chamber and a thermally insulating region adjacent the chamber to prevent heat loss from the chamber through the thermally insulating region. Preferably the at least one sample processing chamber is one or both of a nucleic acid amplification chamber and a nucleic acid detection chamber (hence forth 'processing chamber').

Preferably the nucleic acid processing chamber is adjacent a surface (preferably a bottom surface) of the cartridge for accepting heat from an external source, the chamber situated between the thermally insulating region and the surface such that heat passing from the external source through the surface and thence the chamber is not lost out of the other side of the chamber owing to the presence of the thermally insulating region. This arrangement is found to make the change in temperature inside the chamber (for instance when turning the heat source on and off) as fast as possible, which is beneficial for performing rapid PCR, for example.

This is particularly advantageous because a single heat source may be placed adjacent the cartridge to supply heat for the amplification process from one side (the heated side), and yet the sample within the cartridge will be heated substantially and the amount of heat lost through the unheated side minimised as far as possible.

Preferably the cartridge is comprised of at least a fluidic layer and a pneumatic layer in contacting arrangement. The nucleic acid processing chamber may be formed in the fluidic layer and the thermally insulating region may be formed in the pneumatic layer. Preferably the fluidic cartridge further comprises a fluidic foil underneath the fluidic layer, the foil forming the aforementioned surface for accepting heat. The use of a thin foil maximises the heat transfer from the external source. The material of the foil may be chosen to optimise the heat transfer. For instance, a metal foil may be used, but it is preferred that a polyethylene terephthalate/polypropylene composite is used due to the advantages in ease of manufacture of the cartridge, together with material strength and acceptable heat transfer properties.

Preferably the thermally insulating region is formed from one or more sealed thermal isolation pockets formed in the pneumatic layer and sealed by a pneumatic foil. The pockets may be filled with gas such as air or may be evacuated during the manufacturing process such that they provide a vacuum.

A preferred embodiment of this aspect will now be described with reference to the exemplary fluidic cartridge. As shown in FIG. 3, the exemplary cartridge 100 comprises, from top to bottom, a housing 111, a blister sub-assembly 112, a pneumatic foil 113, a pneumatic layer 114, a fluid layer 115 and a fluidic foil 116.

Referring to FIGS. 6A and 6B, which shows the pneumatic layer, six thermally insulating regions 140a-b, 141a-d are provided. The insulating regions 140a-b are located adjacent two corresponding amplification chambers formed in the fluidic layer 115, whilst insulating regions 141a-d are located adjacent four corresponding detection chambers formed in the fluidic layer 115, when the cartridge is assembled. As shown, the insulating regions 140a-b consist of a plurality of thermal isolation pockets, whereas insulating regions 141a-d each consist of a single pocket.

During nucleic acid amplification and detection, thermocycling of the amplification and detection chambers takes place. The chambers in the fluidic layer may be heated by applying heat to the bottom of the cartridge 100, adjacent the fluidic layer 115. The thermal isolation pockets retain the heat within the cartridge, minimising heat loss from the fluidic layer 115 into the pneumatic layer 114. The thermal isolation pockets also eliminate the need for heating of the fluidics cartridge from both the top and bottom surfaces e.g. heating both the fluidics layer and the pneumatic layer, simplifying the overall design of the cartridge and reader.

The thermal isolation pocket may comprise one large pocket or multiple smaller pockets. The advantage of using multiple smaller pockets is that the risk of convection currents being set up is reduced, thus providing maximal thermal insulation.

2.5 Capture Column

An advantageous arrangement for a filtering device in a fluidic cartridge (preferably a 'capture column') will now be described, which may form an isolated inventive aspect.

Hence, in one aspect, there is provided a fluidic cartridge comprising a channel through which a liquid sample may pass, the channel having a filter for capturing biological components and further comprising:

an upstream portion and a downstream portion; and
a capture portion between the upstream and downstream portions in which the filter is arranged; wherein:
the diameter of the capture portion is greater than the diameter of the upstream and downstream portions.

Preferably the capture portion is a chamber within the channel, the chamber having an inlet surface having an opening coupled to the upstream portion of the channel and an outlet surface having an opening coupled to the downstream portion of the channel.

Preferably the fluidic cartridge comprises at least two polymer layers, wherein the upstream portion and an upstream part of the capture portion of the channel are formed in a first polymer layer and the downstream portion and a downstream part of the capture portion of the channel are formed in a second polymer layer; and wherein the filter is clamped between the first and second polymer layers.

Preferably the inlet surface of the chamber comprises distribution conduits leading radially outwardly from the opening so as to direct a liquid sample passing through the opening in the inlet surface radially outwardly.

Preferably the outlet surface of the chamber comprises distribution conduits leading radially inwardly toward the opening so as to direct a liquid sample which has passed through the filter radially inwardly toward the opening in the outlet surface.

Figure 14A:
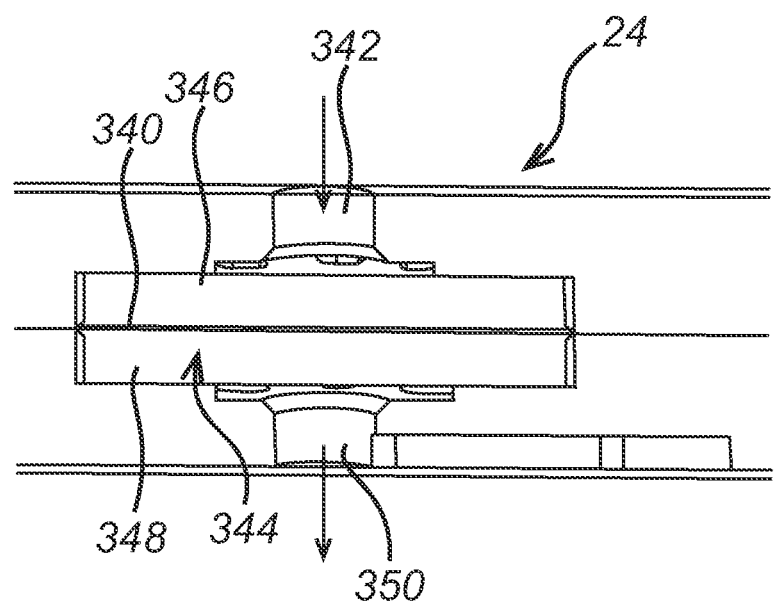
FIG. 14a is a section view of an advantageous capture column arrangement which may form an isolated inventive aspect.
Figure 14B:
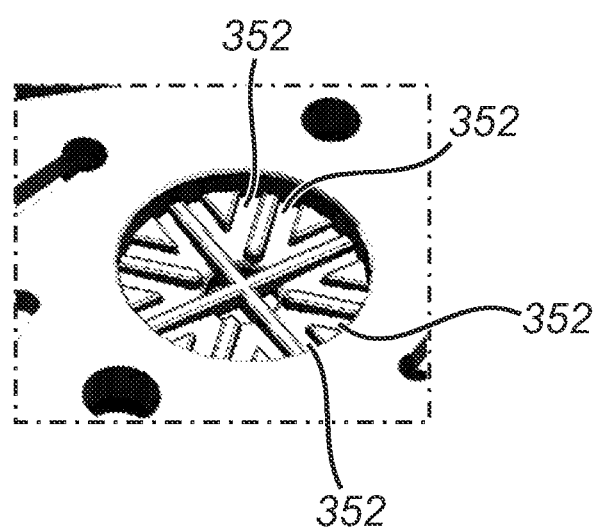

A preferred embodiment of this aspect will now be described with reference to the exemplary fluidic cartridge. In the exemplary cartridge described herein, a capture column 24 is provided along the main channel (see FIG. 1). As shown in FIGS. 14a and 14b, the capture column 24 has filter 340 which binds DNA from lysed material before releasing it during elution. As shown in FIG. 14a, capture column 24 comprises an inlet channel 342 leading into a capture chamber 344 at an upstream end 346, and an outlet channel 350 leading from capture chamber 344 at a downstream end 348.

A filter 340 is provided in chamber 344, perpendicular to the direction of flow of fluid through the main channel, such that fluid must pass through filter 340 when passing from the upstream end of the main channel 342 to the downstream end 350 of the main channel.

Referring now to FIG. 14b, the inlet and outlet walls (only one is shown) of the chamber comprise distribution conduits 352 configured to direct fluid radially outwardly into the chamber 344 as it enters the chamber, and radially inwardly toward the exit aperture after it has passed through the filter 340.

2.6 Waste Chamber

An advantageous arrangement for waste chamber in a fluidic cartridge will now be described, which may form an isolated inventive aspect.

Hence, in one aspect, there is provided a fluidic cartridge comprising a channel through which a liquid sample may pass and a waste chamber for receiving fluid from the channel, the waste chamber comprising:

a pipe, coupled to the channel, extending from a bottom surface of the waste chamber and having an opening elevated above the bottom surface to pass fluid from the channel into the chamber; and
a vent within the waste chamber configured to vent the waste chamber to atmosphere.

Preferably the vent comprises a second pipe, coupled to a vent channel within the cartridge, extending from the bottom surface of the waste chamber and having an opening elevated above the bottom surface. Preferably the vent passageway comprises at least one Anderson impactor.

Preferably at least one absorbent pad is provided within the waste chamber.

A preferred embodiment of this aspect will now be described with reference to the exemplary fluidic cartridge. In the exemplary cartridge described herein, a waste chamber is provided for collecting and storing waste fluid which is produced during washing etc. Waste chamber 10 is shown in more detail in FIGS. 15a and 15b. Waste chamber 38 comprises a pipe 360, extending substantially vertically from a bottom surface 362 of waste chamber 38. The pipe 38 defines a channel having a first end 364 connected to the bottom surface of the waste chamber 38 and fluidly connected to the main channel 16. A second end 366 of fluid pipe 360 is disposed within waste chamber 38, and has an opening through which fluid can flow into the waste chamber.

Figure 15A:
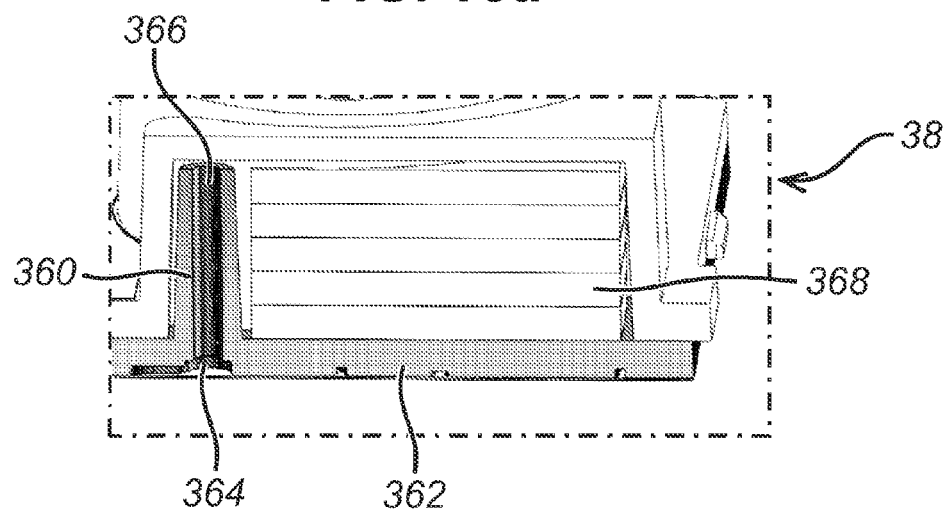
FIG. 15a is a section view of an advantageous waste chamber arrangement which may form an isolated inventive aspect.
Figure 15B:
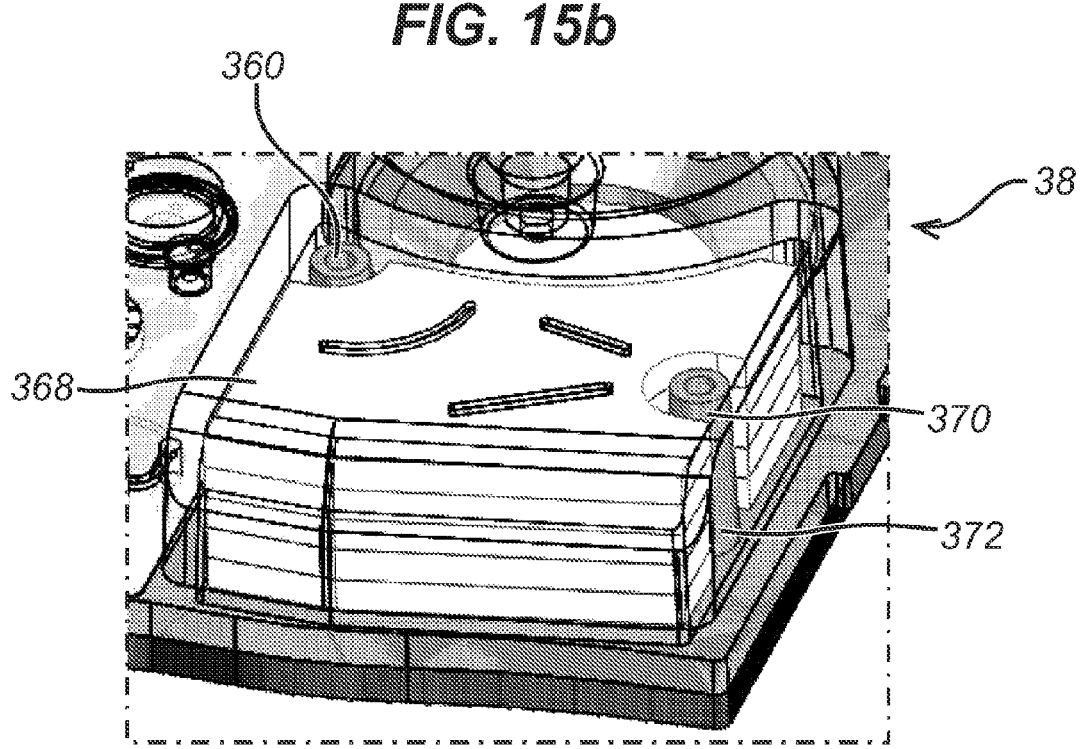

Preferably, pipe 360 is substantially vertical, and perpendicular to the bottom surface of the waste chamber 38. The opening at the second end of pipe 360 is located near the top of the waste chamber 38 as shown in FIG. 15b. By providing the first opening near the top of the waste chamber, the risk of leakage is minimised should the cartridge be turned upside down.

Absorbent pads 368 are also provided in the waste chamber. Preferably, the upper surface of absorbent pads 368 should also be near the top of waste chamber 38, even more preferably, the top of absorbent pads 368 should be substantially level with the opening at the second end 366.

In the exemplary cartridge described herein, a second opening 370 is provided in waste chamber 38 as shown in FIG. 15b. The second opening 370 is configured to vent main channel 16 via waste chamber 28 to atmospheric pressure. This avoids putting a back pressure along the main channel as the waste channel fills with fluid. Preferably, the second opening 370 is provided at the end of a second pipe 372 protruding from the bottom surface of waste chamber 38. The second opening 370 may be fluidly connected to a vent passageway (not shown) which has an opening outside of the cartridge housing to allow the waste chamber to remain at atmospheric pressure. However, venting the waste chamber outside the cartridge carries a small risk of aerosol contamination. To reduce this, the vent path has impact traps and vents under the cartridge cover.

The skilled person will be capable of modifying the exemplary cartridge to implement the inventive aspects described herein in various ways depending on circumstances. It is intended that the scope of the present invention is defined by the following claims.

The invention claimed is:

1. A cartridge for assay of a target nucleic acid sequence in a liquid sample comprising a plastic housing enclosing:
   a. a plastic fluidic portion comprising a channel fluidly connecting a sample inlet to at least one amplification chamber where nucleic acid amplification can take place; a channel fluidly connecting the amplification chamber to at least one detection chamber where the results of nucleic acid amplification can be electrochemically detected; an exhaust; and a gas inlet connectable to a gas supply which is capable of pushing the sample downstream through the cartridge,
   wherein the channels and/or chambers comprise at least one pneumatically controlled valve,
   and wherein upstream of the amplification chamber are provided: reagents and/or physical components for cell lysis and nucleic acid separation; in or upstream of the amplification chamber, but downstream of the reagents and/or physical components for cell lysis and nucleic acid separation, are provided reagents for nucleic acid amplification including a nucleic acid polymerase; and in or upstream of the detection chamber, but downstream of the amplification chamber, are provided reagents for electrochemical nucleic acid detection;
   b. a plastic pneumatic portion comprising at least one pneumatic pressure inlet and pneumatic circuit for conveying pneumatic pressure;
   whereby flow through the channels and chambers can be controlled by the pneumatic pressure applied to the at least one pneumatically controlled valve; and
   c. at least two electrodes capable of providing a potential difference across the at least one detection chamber for permitting detection of electrochemically active molecules.

2. The cartridge of claim 1, wherein the fluidic portion further comprises a control nucleic acid.

3. The cartridge of claim 2, wherein the control nucleic acid is DNA.

4. The cartridge of claim 1, wherein the target nucleic acid is DNA.

5. The cartridge of claim 4, wherein the target DNA is from a pathogen.

6. The cartridge of claim 1, wherein the reagents for nucleic acid amplification further comprise primers capable of hybridizing to the target nucleic acid sequence, dNTPs, and optionally further comprises one or more of buffer salts, MgCl2, passivation agents, uracil N-glycosylase and dUTP.

7. The cartridge of claim 2, wherein the reagents for nucleic acid amplification further comprise primers capable of hybridizing to the control nucleic acid.

8. The cartridge of claim 1, wherein the reagents for electrochemical nucleic acid detection comprise at least one target probe comprising a label, wherein the target probe is capable of specifically hybridizing to the target molecule.

9. The cartridge of claim 2, wherein the reagents for electrochemical nucleic acid detection comprise at least one control probe comprising a label, wherein the control probe is capable of specifically hybridizing to the control molecule.

10. The cartridge of claim 8, wherein the label is a ferrocene label.

11. The cartridge of claim 1, wherein the reagents for nucleic acid detection comprise a 5' to 3' exonuclease.

12. The cartridge of claim 1, wherein the pneumatic portion comprises multiple pneumatic pressure inlets each of which controls flow through separate regions of the fluidic portion.

13. The cartridge of claim 1, wherein flow through the channels and chambers is controlled by multiple pneumatically controlled valves.

14. The cartridge of claim 1, wherein the fluidic portion further comprises a coarse filter downstream of the sample inlet and upstream of the reagents and/or physical components for cell lysis and nucleic acid separation.

15. The cartridge of claim 1, wherein the reagents and/or physical components for cell lysis and nucleic acid separation include lysis buffer.

16. The cartridge of claim 1, wherein the reagents and/or physical components for cell lysis and nucleic acid separation include a nucleic acid capture column.

17. The cartridge of claim 1, wherein the fluidic portion further comprises one or more of a sample mixing chamber, a sample indicator, a bellows, a mixing channel, a blister sub-assembly, an isolation valve, an elution chamber.

18. The cartridge of claim 1, wherein the plastic fluidic portion comprises polypropylene.

19. The cartridge of claim 1, wherein the plastic pneumatic portion comprises polypropylene.

20. The cartridge of claim 1, wherein the plastic housing comprises acrylonitrile butadiene styrene.

* * * * *